United States Patent
Ewing et al.

(10) Patent No.: US 7,130,675 B2
(45) Date of Patent: Oct. 31, 2006

(54) HIGH-RESOLUTION MAGNETOENCEPHALOGRAPHY SYSTEM AND METHOD

(75) Inventors: Anthony P. Ewing, San Diego, CA (US); Yoshio Okada, Albuquerque, NM (US); Douglas N. Paulson, Del Mar, CA (US); Tatiana N. Starr, San Diego, CA (US)

(73) Assignee: Tristan Technologies, Inc., San Diego, CA (US)

( * ) Notice: Subject to any disclaimer, the term of this patent is extended or adjusted under 35 U.S.C. 154(b) by 158 days.

(21) Appl. No.: 10/608,725

(22) Filed: Jun. 26, 2003

(65) Prior Publication Data

US 2004/0002645 A1   Jan. 1, 2004

Related U.S. Application Data

(60) Provisional application No. 60/393,045, filed on Jun. 28, 2002.

(51) Int. Cl.
*A61B 5/05* (2006.01)
(52) U.S. Cl. ........................ 600/409; 324/248
(58) Field of Classification Search ................ 600/409; 324/244, 248, 256, 257, 260, 261
See application file for complete search history.

(56) References Cited

U.S. PATENT DOCUMENTS

| | | | | |
|---|---|---|---|---|
| 4,951,674 A | * | 8/1990 | Zanakis et al. ............. | 600/409 |
| 4,996,479 A | * | 2/1991 | Hoenig ....................... | 324/248 |
| 5,036,279 A | * | 7/1991 | Jonsen ....................... | 324/307 |
| 5,166,614 A | * | 11/1992 | Yokosawa et al. .......... | 324/248 |
| 5,193,348 A | * | 3/1993 | Schnapper .................. | 62/51.1 |
| 5,309,095 A | * | 5/1994 | Ahonen et al. ............. | 324/248 |
| 5,442,289 A | * | 8/1995 | DiIorio et al. .............. | 324/248 |
| 5,475,306 A | * | 12/1995 | Ludeke et al. .............. | 324/248 |
| 2004/0173221 A1 | * | 9/2004 | Singhal et al. .............. | 128/898 |
| 2004/0254443 A1 | * | 12/2004 | Gott et al. .................. | 600/409 |

OTHER PUBLICATIONS

Choi et al. "Noninvasive determination of the optical properties of adult brain: near-infrared spectroscopy approach" (Feb. 2004) Journal of Biomedical Optics 9(1), 221-229.*

* cited by examiner

*Primary Examiner*—Ruth S. Smith
(74) *Attorney, Agent, or Firm*—Duckor Spradling Metzger & Wynne; Bernard L. Kleinke

(57) ABSTRACT

According to certain embodiments of the present invention, there is provided a magnetoencephalography and method employing a portable cart having a SQUID dewar mounted in an inverted manner thereon, and having a headrest assembly mounted on the cart for supporting the head of a patient and forming a portion of the dewar. The headrest assembly includes an array of magnetic sensors of the SQUID dewar for responding to electrical activity of the brain of the head.

25 Claims, 28 Drawing Sheets

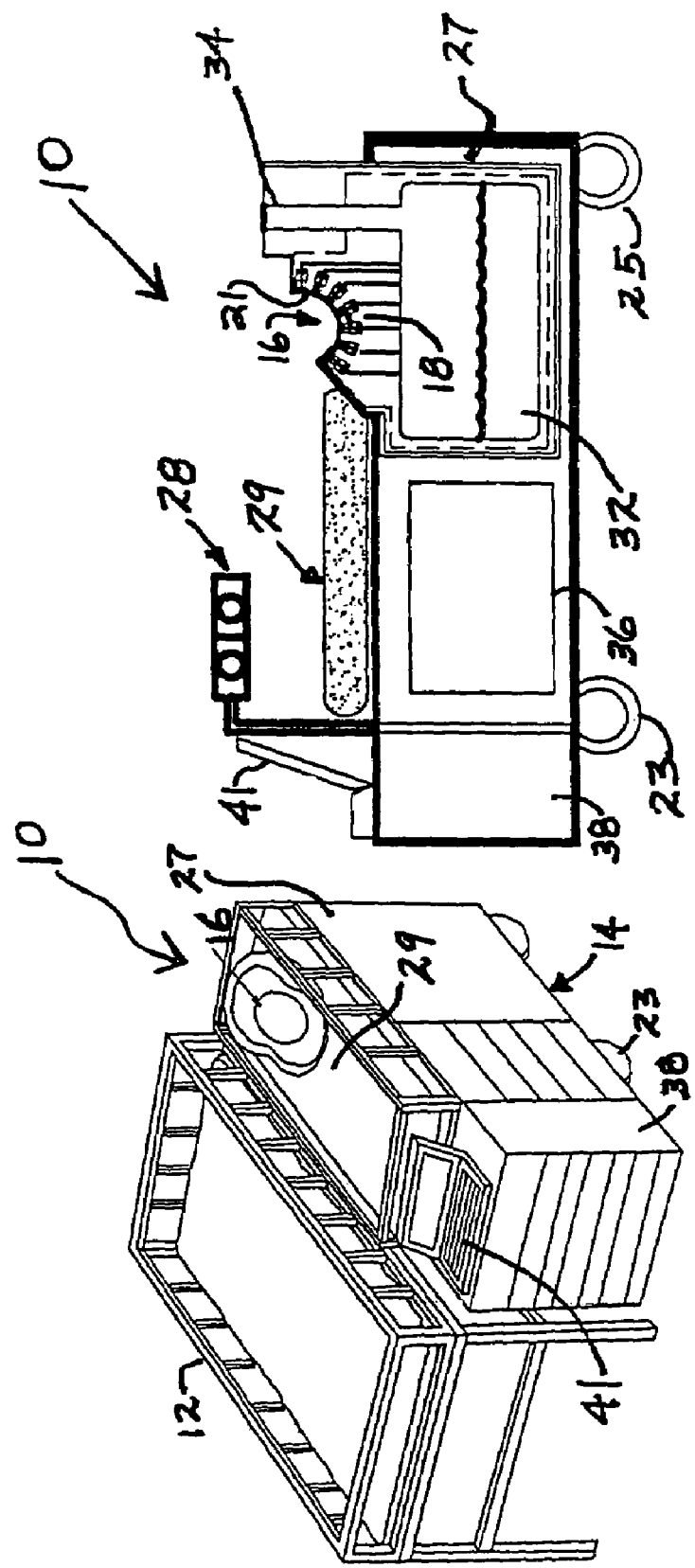

Module Layout

Four Channel Module

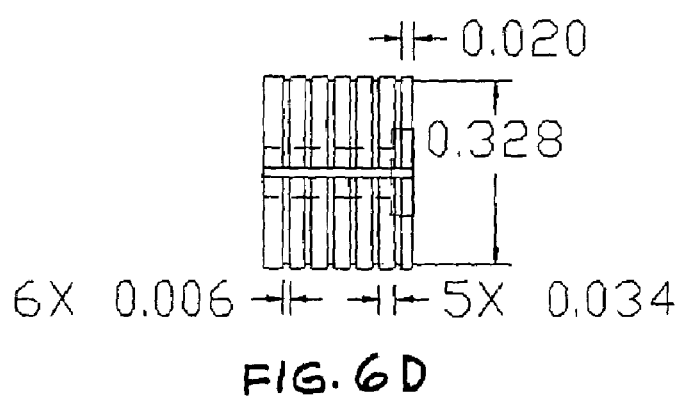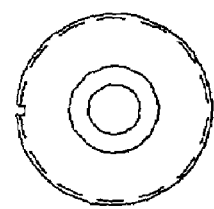
FIG. 6D
FIG. 6E

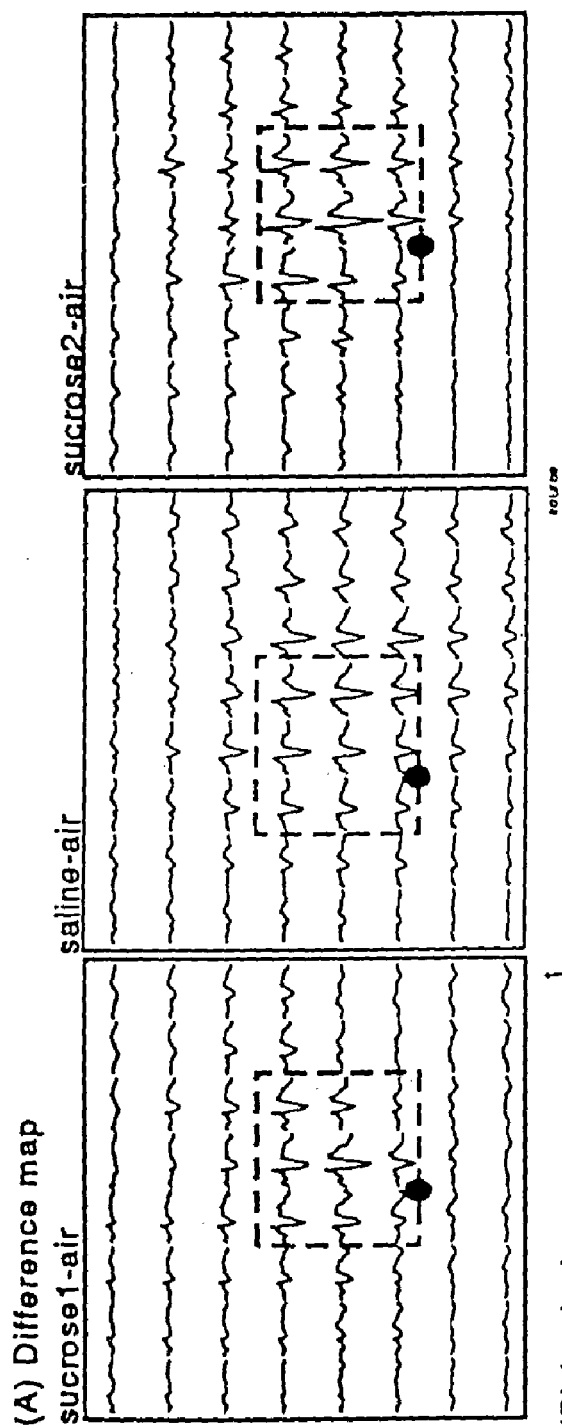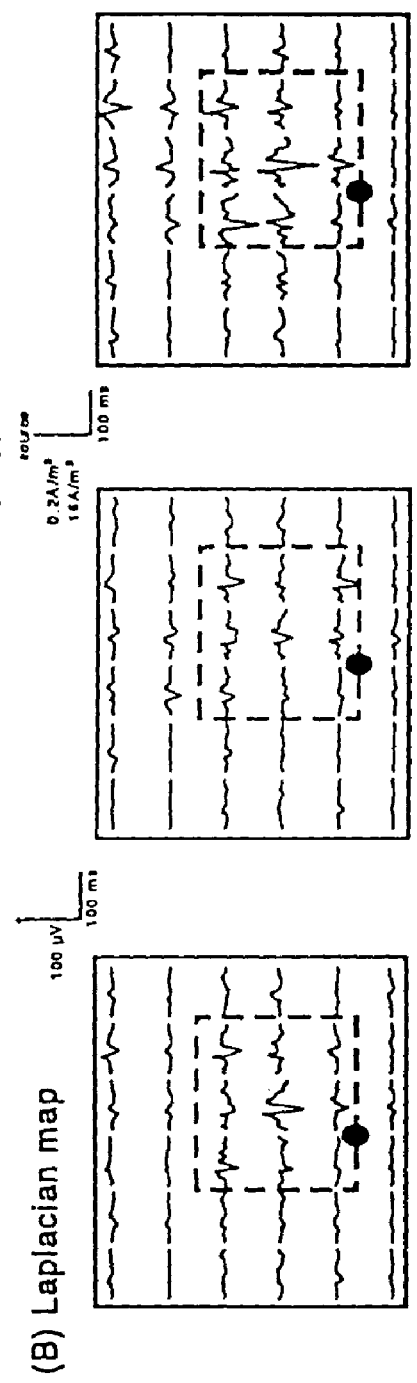
FIG. 13A
FIG. 13B

HIGH-RESOLUTION MAGNETOENCEPHALOGRAPHY SYSTEM AND METHOD

RELATED APPLICATIONS

The present application is related to U.S. patent application entitled "HIGH-RESOLUTION MAGNETOENCEPHALOGRAPHY SYSTEM, COMPONENTS, AND METHOD," filed Jun. 26, 2003, Ser. No. 10/609,259, which is incorporated herein by reference.

The subject patent application claims priority to U.S. provisional patent application, entitled HIGH-RESOLUTION MAGNETOENCEPHALOGRAPHY SYSTEM, Ser. No. 60/393,045, filed Jun. 28, 2002, which is incorporated herein by reference.

BACKGROUND OF THE INVENTION

1. Field of the Invention

The invention relates to medical diagnostic systems and methods. In particular, the invention relates to a system and method for obtaining high-resolution encephalographs.

2. Related Art

The information contained in this section relates to the background of the art of the present invention without any admission as to whether or not it legally constitutes prior art.

The following is a list of articles relating to various diagnostic techniques contemplated for assessing brain functions, as follows:

Ahonen, A. I., Hamalainen, M. S., Kajola, M. J., Knuutila, J. E. T., Laine, P. P., Lounasmaa, O. V., Parkkonen, L. T., Simola, J. T., and Tesche, C. D. 122 channel SQUID instrument for investigating the magnetic signals from the human brain. Physica Scripta, 1993, T49: 198–205;

Barth, D. S., Sutherling, W., Broffman, J., and Beatty, J. Magnetic localization of a dipolar current source implanted in a sphere and a human cranium. Electroenceph. clin. Neurophysiol., 1986, 63: 260–273;

Buchanan, D. S., Crum, D. B., Cox, D., & Wikswo, J. P. jr. MicroSQUID: A close-spaced four channel magnetometer. In S. J. Williamson et al., (eds.), Advances in Biomagnetism, Plenum Press, New York, 1989, pp. 677–679;

Curio, G., Mackert, B. -M., Abraham-Fuchs, K., and Härer, W. (1994) High-frequency activity (600 Hz) evoked in the human primary somatosensory cortex: a survery of electric and magnetic recordings. In C. Patev et al., eds. Oscillatory Event-Related Brain Dynamics, Penum Press, New York, pp. 205–218;

Curio, G., Mackert, B. -M., Burghoffm M., Koetitz, R., Abraham-Fuchs, K., and Hätrer, W. (1994) Localization of evoked neuromagnetic 600 Hz activity in the cerebral somatosensory system. Electroenceph. cdin. Neurophysiol., 91:483–487;

De Weerd, A. W. Atlas of EEG in the first months of life. El Sevier, New York, 1995;

Dreyfus-Brisac, C. The electroencephalogram of the premature infant and full-term newborn: normal and abnormal development of waking and sleeping patterns. In P. Kellaway and I. Petersén (eds.), Neurological and electroencephalographic correlative studies in infancy. Grune and Stratton, New York, 1964, pp. 186–207;

Dreyfus-Brisac, C. The electroencephalogram of the premature infant. World Neurol., 1962, 3: 5–15;

Dreyfus-Brisac, C., Samson, D., Blanc, C., and Monod, N. L'electroencéphalogramme de l'enfant normal de moins de 3 ans. Etud. néo-natal. 1958, 7: 143–175;

Emerson, R. G., Sgro, J. A., Pedley, T. A., Hauser, W. A. (1988) State-dependent changes in the N20 component of the median nerve somatosensory evoked potential. Neurology, 38: 64–68.

Erasmie, U., & Ringertz, H. Normal width of cranial sutures in the neonate and infant. Acta Radiol. Diagnosis, 1976,17: 565–572;

Geselowitz, D. B. On the magnetic field generated outside an inhomogeneous volume conductor by internal current sources. IEEE Trans. Mag., 1970, 6: 346–347;

Gevins, A., Le, J., Leong, H., McEvoy, L. K., and Smith, M. E. (1999) Deblurring. J. Clin. Neurophysiol. 16: 204–213;

Gevins, A., Le, J., Martin, N. K., Brickett, P., Desmond, J., and Reutter, B. High resolution EEG: 124-channel recording, spatial deblurring and MRI integration methods. Electroenceph. clin. Neurophysiol., 1994, 90: 337–358;

Gobbelé, R., Buchner, H., and Curio, G. (1998) High-frequency (600 Hz) SEP activities originating in the subcortical and cortical human somatosensory system. Electroenceph. clin. Neurophysiol., 108: 182–189;

Goff, W. R., Allison, T., and Vaughan, H. G., Jr. (1978) The functional neuroanatomy of event related potentials. In: Event-related brain potentials in man. E. Callaway, P. Tueting, and S. H. Koslow (Eds.), Academic Press, New York San Francisco London, pp. 1–79;

Grynszpan, F. and Geselowitz, D. B. (1973) Model studies for the magnetocardiogram. Biophys. J., 13: 911–925;

Hämäläinen, M. S., and llmoniemi, R. (1994) Interpreting magnetic fields of the brain: minimum norm estimates. Med. Biol. Eng. Comp., 32:35–42;

Hämätäinen, M. S., and Sarvas, J. (1989) Realistic conductivity geometry model of the human head for interpretation of neuromagnetic data. IEEE Trans. Biomed. Eng., 36:165–171;

Hämäläinen, M., and Sarvas, J. Realistic conductivity geometry model of the human head for interpretation of neuromagnetic data. IEEE Trans. Biomed. Eng., 1989, 36: 165–171;

Hansman, C. F. (1966) Growth of interorbital distance and skull thickness as observed in roentgenographic measurements. Radiology, 86:87–96;

Hansman, C. F. Growth of interorbital distance and skull thickness as observed in roentgenographic measurements. Radiology, 1966, 86: 87–96;

Hashimoto, I., Mashiko, T., and Imada, T. (1996a) Somatic evoked high-frequency magnetic oscillations reflect activity of inhibitory interneurons in the human somatosensory cortex. Electroenceph. clin. Neurophysiol., 100:189–203;

Hashimoto, I., Papuashvili, N., Xu, C. and Okada, Y. C. (1996b) Neuronal activities from a deep subcortical structure can be detected magnetically outside the brain in the porcine preparation. Neurosci. Lett. 206:25–28;

Haueisen, J., Heuer, T., Nowak, H., Liepert, J., Weiller, C., Okada, Y. C., and Curio, G. (2000a) The influence of lorazepam on somatosensory evoked fast frequency (600 Hz) activity in MEG. Brain Res. in press;

Haueisen, J., Schack, B., Meier, T., Nowak, H., Weiller, C., Curio, G., and Okada, Y. C. (2000b) Time-frequency analysis of somatosensory evoked short latency cortical activity in MEG. To be submitted to Clinical Neurophysiology;

Humphrey, D. R. (1 968a) Re-analysis of the antidromic cortical response. I. potentials evoked by stimulation of the isolated pyramidal tract. Electroenceph. clin. Neurophysiol., 24:116–129;

Humphrey, D. R. (1968b) Re-analysis of the antidromic cortical response. II. on the contribution of cell discharge and PSPs to the evoked potentials. *Electroenceph. clin. Neurophysiol.*, 25:421–442;

Kaufman, L., Okada, Y., Brenner, D., and Williamson, S. J. (1981) On the relation between somatic evoked potentials and fields. *Int. J. Neurosci.*, 15: 223–239;

Le, J., Menon, V., and Gevins, A. Local estimate of surface Laplacian derivation on a realistically shaped scalp surface and its performance on noisy data. *Electroenceph. clin. Neurophysiol.*, 1994, 92: 433–441;

Lusted, L. B., and Keats, T. E. *Atlas of roentgenographic measurement*. Year Book Publishers, Chicago, 1978;

Mackert, B. -M., Weisenbach, S., Nolte, G., and Curio, G. (2000) Rapid recovery (20 ms) of human 600 Hz electroencephalographic wavelets after double stimulations of sensory nerves. Neurosci. Lett., 286:83–86;

Okada Y C, Läthteenmäki A, Xu C (1999a) Comparison of MEG and EEG on the basis of somatic evoked responses elicited by stimulation of the snout in the juvenile swine. Clin Neurophysiol 110:214–229;

Okada Y C, Lahteenmaki A, Xu C (1999b) Experimental analysis of distortion of magnetoencephalography signals by the skull. Clin Neurophysiol 110:230–238;

Okada Y C, Shah B, Huang J -C (1994) Ferromagnetic high-permeability alloy alone can provide sufficient low-frequency and eddy-current shieldings for biomagnetic measurements. IEEE Trans Biomed Eng 41:688–697;

Okada, Y. C., Shah, B. and Huang, J. -C. (1994) Ferromagnetic high-permeability alloy alone can provide sufficient low-frequency and eddy-current shieldings for biomagnetic measurements. *IEEE Trans. BME*, 41: 688–697;

Roark, R. J. and Young, W. C. *Formulas for stress and strain.* McGraw-Hill, New York, 1975;

Sunshine, P. Epidemiology of perinatal asphyxia. In: D. K. Stevenson and P. Sunshine, (eds.), *Fetal and neonatal brain iniury: Mechanisms, management and the risks of practice*. Oxford Univ. Press, New York, 1997, pp. 3–23;

Sunshine, R. (1997) Epidemiology of perinatal asphyxia. In: D. K. Stevenson and P. Sunshine, (eds.), *Fetal and neonatal brain iniurv: Mechanisms, management and the risks of practice*. Oxford Univ. Press, New York, pp. 3–23;

Tharp, B. Use of the electroencephalogram in assessing acute brain damage in the newborn. In: D. K. Stevenson and P. Sunshine, (eds.), *Fetal and neonatal brain iniury: Mechanisms, management and the risks of practice*. Oxford Univ. Press, New York, 1997, pp. 287–301;

Volpe, J. J. *Neurology of the new born*. W. B. Sanders, Philadelphia, Pa., 2000; and Yamada, T., Kameyama, S., Fuchigami, Y., Nakazumi, Y., Dickens, Q. S., and Kimura, J. (1988) Changes of short latency somatosensory evoked potential in sleep. *Electroenceph. clin. Neurophysiol.*, 70: 126–136. The foregoing articles are each incorporated herein by reference.

The need for finding useful diagnostic techniques is becoming increasingly urgent today in assessing brain functions of infants. With advances in medicine, more and more pre- and full-term newborns survive even with neurological disabilities (Sunshine, 1997; Volpe, 2000). According to Sunshine (1997), the number of newborns with neurological impairments is quite large. The incidence of perinatal asphyxia is between about 2/1000 and about 47/1000. Between about 4% and about 26% of those newborns who survive such an event will have severe neurological deficits. The incidence of hypoxemic-ischemic encephalopathy in term or near-term infants is between about 3/1000 and 8/1000. Handicapped survivors may be as high as about 42% in such cases. The incidence of infants with neonatal seizures is between about 2/1000 and about 9/1000. The incidence of handicaps in the survivors is between about 11% and about 50%. The incidence of moderate-to-severe cerebral palsy in infants who survive the neonatal period is between about 1/1000 and 3/1000. The prevalence of severe mental retardation is between about 3/1000 and about 4/1000 school-age children. The incidence of mild mental retardation is between about 23/1000 and about 30/1000 in the same population. According to Volpe (2000), the percentage of preterm infants with proven periventricular white matter injury is about 45% for those with birth weight of less than about 1500 g, about 38% for those with gestational age of less than about 33 weeks and about 24% for those with gestational age of less than about 38 weeks. The percentage of asphyxiated term infants with some form of central nervous system injury is as high as about 62%, a common form of the injury being the parasagittal cerebral injury. Infants with germinal matrix hemorrhage is between about 23% and about 32% of all births delivered through the vaginal route when the delivery lasts more than six hours.

Survival of neurologically impaired neonates raises an important responsibility for the health care community in this country. Currently, electroencephalography (EEG) is used to monitor electrical activity of the brain of newborns (Sunshine, 1997). The use of EEG for perinatal monitoring was started in the late 1950's (Dreyfus-Brisac et al., 1958; Dreyfus-Brisac, 1962, 1964). Its use is increasing in recent years due to its usefulness in staging the development of the nervous system, in detecting the presence of hypoxic and intracranial injuries, in providing the prognosis of recovery and in differential diagnosis of seizures from non-seizures in paroxysmal motor behavior (Tharp, 1997; de Weerd, 1995). The staging is useful in detecting a delay or an arrest in brain development. The waveforms and spatial topography such as hemispheric asymmetry of spontaneous EEG are also useful for detecting the presence of a tumor or a necrotic area in the brain.

In order for magnatoencephalography (MEG) to become useful as a clinical electrophysiological monitoring technique, complementing EEG, it may be desirable for certain applications to have a MEG instrument which may be different from the conventional whole-head MEG instruments. In this regard, to be competitive with EEG instrumentation, a useful MEG instrument must be functional in any ordinary clinical rooms without any special cumbersome electromagnetic shielding such, for example, as a large and expensive, special purpose magnetically shielded room being currently used when conventional MEG techniques are employed.

Prior known MEG systems (such as those manufactured by Canadian Thin Films or CTF, Vancouver, Canada, 4-D Neuroimaging, San Diego, Calif., and Helsinki, Finland) are relatively large and heavy, and are used mostly in an expensive magnetically shielded room.

BRIEF DESCRIPTION OF THE DRAWINGS

FIG. 1A is a diagrammatic illustration of a high-resolution magneto-encephalography (MEG) system according to one embodiment of the present invention;

FIG. 1B is a diagrammatic cross-sectional side view of the system illustrated in FIG. 1A;

FIG. 6D and 6E illustrates a coil form for the cancellation coil of the module illustrated in FIGS. 5A, 5B and 5C;

FIG. 13A illustrates charts showing the distortions due to conductivity differences;

FIG. 13B illustrates charts illustrating the Laplacian estimates of currents emerging through a filter paper for various conditions;

DESCRIPTION OF CERTAIN EMBODIMENTS OF THE INVENTION

Figure 2A:
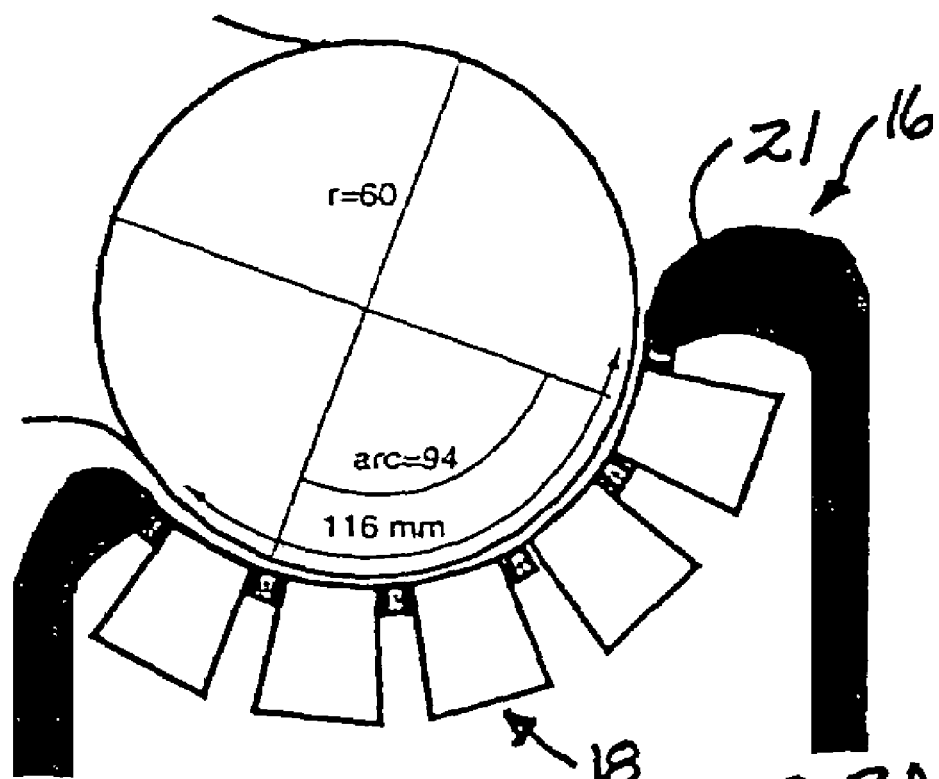
FIG. 2A is a cross-sectional diagrammatic view of one embodiment of the headrest assembly of the system of FIG. 1A.

According to certain embodiments of the present invention, there is provided a magnetoencephalography system and method employing a portable cart having a SQUID dewar mounted in an inverted manner thereon, and having a headrest assembly mounted on the cart for supporting the head of a patient and forming a portion of the dewar. The headrest assembly includes an array of magnetic sensors of the SQUID dewar for responding to electrical activity of the brain of the head. The dewar is inverted in that its sensors are disposed above its reservoir.

Referring now to the drawing and more particularly to FIGS. 1A and 1B thereof, the disclosed embodiments of the present invention relates to a high-resolution magnetoencephalography (MEG) system 10 for evaluating neurological impairments of preterm and term babies, for example. The system 10 provides a non-invasive neurodiagnostic tool that may complement electroencephalography (EEG) in assessing possible neurological dysfunctions and brain development in neonates through its capability to detect electrophysiological functions in focal areas of the cortex in real time with or preferably without signal averaging.

The system 10 is a portable, non-invasive MEG system that can be used next to a crib 12 of any neonatal care unit without a cumbersome magnetically shielded room (not shown). The system 10 includes a cart 14 which may be the size and shape of an examination table with a headrest assembly 16 for receiving the head of a patient (not shown). Desirable spatial resolution and sensitivity may be provided by a closely-spaced evenly-distributed array (e.g., 19×4-channel modules) of superconducting MEG sensors 18 housed below the outer surface of a headrest 21 (FIG. 1B) of the headrest assembly 16. For example, the sensors may be housed between about 1 mm and about 3 mm below the outer surface. The sensors may be protected against radio frequency (rf) noise. The entire system is light enough to be portable, and the cart 14 includes wheels such as wheels 23 and 25 for rollably supporting the cart on the ground.

A dewar 27 of a superconducting quantum interference device (SQUID) is mounted in an inverted manner on the cart 14. A patient bed or cushion 29 is mounted on the cart 14 adjacent to the headrest assembly 16 for supporting the body of the patient with his or her head supported by the headrest.

The SQUID dewar 27 includes a liquid helium reservoir 32 and a fill port 34. A SQUID phase lock loop electronic circuits and routers unit 36 control the SQUID functions and are used for data acquisition. The unit 36 is mounted on cart 14. A computer and power supply unit 38 is mounted at the rear end of the cart 14. A monitor and keyboard unit 41 are mounted above the unit 38 and communicate electrically therewith.

A short sensor distance combined with improved sensor noise provide unprecedented sensitivity and spatial resolution for infant studies. The system 10 may be about one order of magnitude better in sensitivity than the conventional whole-head MEG sensors (e.g. Ahonen et al., 1992; Buchanan et al., 1994). Its sensitivity may be sufficiently high to measure not only spontaneous neuronal activity, but also evoked activity of the cortex of the newborns in real time preferably without signal averaging. Its spatial resolution system 10 will be greater by a factor of about four in comparison to the existing whole-head MEG sensors.

The system 10 takes advantage of the fact that the infant's scalp and skull are thin. This make it possible to measure MEG signals at a distance of only between about 5 mm and about 6 mm from the brain surface. This short distance results in a very large amplitude of MEG signals from the newborns, since the magnetic field is inversely proportional to the square of the distance. The short distance and a high density of detectors also result in high spatial resolution.

It has been determined that a 4-channel module with a noise level less than 10 fT/$\sqrt{Hz}$ for detection coils with a diameter of about 6 mm can be built. Further, the headrest 21 can have a thickness of about 1.0 mm or only slightly greater and is safe to use for the system 10 (i.e., that holds the vacuum without breakage) can be constructed. The sensitivity of the system 10 should be high enough to clearly detect evoked cortical activity preferably without signal averaging In certain embodiments of the invention, the MEG sensors are housed in a vacuum section just below the headrest assembly 16. The wall of the headrest is thin (about 1 mm or only slightly greater) so that the detection coils of the sensors can be placed as close to the head as possible (~2 mm).

The sensor array 18 of one embodiment of the system 10, includes of 19 modules, each module having 4 channels of sensors. It will be understood hereinafter described in greater detail, the sensors can be arranged in clusters in accordance with another embodiment of the invention. Such modules can be fabricated with a noise level of less than 10 fT/$\sqrt{Hz}$ for sensor pickup coils with a diameter of 6 mm. This is possible even though the cross sectional area of the coils is about 10 times smaller than those of the conventional whole-head sensors.

The sensitivity of the system 10 is sufficiently high to clearly detect evoked cortical activity without signal averaging. A test was carried out by measuring the somatic evoked magnetic fields (SEFs) in 1–7 month old infants with a microSQUID (not shown) which was similar to the system 10 in that it has a 4-channel module in the vacuum space just below the tail section of a conventionally oriented dewar. The distance between the pickup coils and the outer dewar wall surface was very short (about 1.2 mm) and comparable to the distance for the system 10. The noise level of the system 10 may be about 5 to about 6 times better than that of the prior known similar MEG systems. Thus, one can extrapolate from the SEFs measured with the system 10 to infer whether evoked cortical responses can be indeed measured without signal averaging using the system 10. In one embodiment of the invention, clear signals were measured non-invasively by averaging 16 responses to vibratory stimuli and 36 responses to air puffs applied to the tip of the index finger. Extrapolating from these results, it may be concluded that the system 10 is able to clearly detect such SEFs without signal averaging, since the system 10 requires between about 25 and about 36 times less averaging than the prior known similar MEG systems to obtain signals with comparable signal-to-noise ratios.

The system 10 is the size of an ordinary examination table in one embodiment of the invention. The system 10 itself is provided the cart 14 with the mattress or bed 29 on top thereof, adjacent to the headrest. The acquisition of brain signal is relatively rapid, since there is no need to attach electrodes, as in the case, for example, of an EEG. The measurements of MEG signals can start immediately after placing the baby on the bed 29 and the head in the headrest assembly 16. For conventional EEG, placing electrodes on the scalp is time consuming and often troublesome since the baby may easily resist. The baby may wake up if not sedated. This practical problem limits the number of electrodes to be used in any diagnosis, thereby severely limiting the inference that can be made regarding the nature of brain abnormality.

The MEG system 10 is also able to function in clinical rooms without magnetic shielding. An ideal system should function without interference from the ambient magnetic field, line frequency and radio frequency noises, for example. The system 10 may be equipped with SQUID control electronics with, for example, an effective dynamic range of about 32 bits that resolve magnetic fields between about 10 µT and <about 1 fT. It may also have a fast slew rate that can follow magnetic field changes as fast as about 10 µT/ms which is fast enough to follow changes in the line frequency noise without loosing the lock on the flux-locked feedback loop. This fast slew rate enables the system 10 to maintain the SQUIDs operating continuously in the midst of low frequency magnetic field changes and line frequency noises. The short-line baseline gradiometers and the reference channels enable the low frequency and 60 Hz noise to be cancelled with a suppression rate of between about 30 dB and about 90 dB. Thus, the system 10 may operate in unshielded environments.

The above features make the system 10 useful in an ordinary clinical setting. In addition to these features, the MEG system 10 may have a sufficiently high level of sensitivity and spatial resolution to provide new information for certain applications. The system 10 may satisfy this essential requirement by taking advantage of several unique features of the head of infants. First, the skull and scalp of a newborn are quite thin. The human skull at the age of 6 months after birth has an average thickness of about 2.5 mm (minimum of about 1.3 mm, maximum of about 3.7 mm) for girls and about 2.7 mm (minimum of about 1.7 mm, maximum of about 3.8 mm) for boys (Hansman, 1966). Extrapolating from their normative data in connection with certain embodiments of the invention, the skull should be between about 1.7 and about 2.0 mm thick at birth. The scalp is also about 1 mm thick in the first several months of age. Thus, MEG sensing coils can be placed as close as between about 5 and about 6 mm from the cortical surface when the MEG system 10 is built with about a 2 mm distance between the outer surface of the pillowcase and the sensing coils. The system 10 may be thus capable of measuring MEG signals at a distance of about 5 mm as opposed to between about 25 to about 30 mm for the conventional whole-head MEG instruments. Thus, the measurement distance for a cortical source 3 mm below the surface of the brain would be about 8 mm and about 30 mm for the system 10 and a conventional whole-head MEG system. This implies that the signal may be more than 10 times stronger when measured with the system 10. Therefore, it may be possible to monitor cortical activity in real time without signal averaging. Monitoring cortical activity at a distance of about 5 mm also increases spatial resolution. The sensing coils are tightly packed in the system 10 to maximize the spatial resolution. The spatial resolution of the system 10 is about four times higher than that of the conventional whole-head MEG systems. For an example of a whole-head MEG system, reference may be made to U.S. Pat. No. 6,023,633, which is incorporated herein by reference. All sensor coils are assembled below the headrest, so that there is no need to position each sensor precisely as it would be required by EEG if one were to carry out a quantitative EEG analysis. The high-density packing of the sensors in the system 10 make it possible to delineate the abnormal cortical region such as the bilateral strip of cortical tissue along the anterior-posterior direction expected in the case of parasagittal cerebral injury typical of term infants who have suffered a temporary ischemia or anoxia.

Certain embodiments of the system may be capable of measuring cortical activity as if its sensing coils are placed a few millimeters above the cortical surface without the intervening scalp and skull, that is as if the scalp and skull are removed and the sensors lie very close to the exposed cortical surface. The magnetic field above the head is essentially the same as the field present at the cortex except for an attenuation of signal amplitude and spread of the spatial distribution of the magnetic field merely due to the slightly larger distance of measurement. This means that an MEG signal above the scalp should be quite similar in information content to the signal just above the cortex. MEG signals are transparent to the scalp and skull, unlike EEG, even in the presence of skull defects created by the fontanels and sutures. It has been argued that the skull is "transparent" to MEG signals (Kaufman et al., 1981) on the basis of theoretical results obtained by Geselowitz and Grynszpan (Geselowitz, 1970; Grynszpan and Geselowitz, 1973). This conclusion is supported by simulations studies (Hämäläinen and Sarvas, 1989), by measurements of MEG signals outside the head of a cadaver with a hole in the skull (Barth et al., 1986) and by a careful comparison of the topography of the somatic evoked magnetic fields before and after a hole is introduced in the skull in an in vivo piglet study (Okada et al., 1999b, see Phase I Final Report).

In comparison, EEG signals may be significantly distorted by skull defects that are unique to the human neonates. The fontanels are present at the midline junctions of the bregma and lambda. The skull is not present within the fontanels; instead the brain is protected by a thick dura filling the windows. They are small during the delivery, but become larger in the first several months, up to between about 3 cm and about 4 cm along the coronal suture, and then eventually they close. The anterior fontanel may be large enough to admit an adult's thumb. The unclosed sutures can be quite wide near the fontanels. The mean width of the coronal and lambdoidal sutures at their midpositions is 3–4 mm for infants between 0 and about 60 days after birth (Eramie and Ringertz, 1976). In abnormal cases such as hydrocephalous, the sutures may change its width with the development of the disease and become as wide as 10 mm or more (Eramie and Ringertz, 1976). Moreover, the sutures do not close for many years (Hansman, 1966). The earliest age for complete closing of the sagittal and coronal sutures are 6 and 11 years, respectively. Thus, EEG signals may be profoundly affected by the fontanels and sutures since they create paths of low conductivity for the volume currents in the brain and funnels the currents through these openings in the skull.

It might be argued that the skull defects are not a disadvantage for EEG, but on the contrary, are an advantage. In diagnosing seizures the breech provided by the fontanels improves the sensitivity of the EEG. However, the skull defects may obscure the asymmetry of the signals, especially when the generator is deep, making it difficult to determine the epileptiform tissue when it can not be easily visualized by CT or MRI.

The conductivity of the skull is also expected to change with age and across individuals. The skull thickness increases rapidly within the first three years of age from about 2 mm at birth for term newborns to about 5 mm at 3 years of age for boys, then the growth slows down (Hansman, 1966). The skull thickness reaches a mean of about 8.3 mm and about 9.5 mm for 25 year-old women and men, respectively. These changes in skull thickness are associated with thickening of the dense, poorly-conducting inner and outer bony tables of the skull relative to the spongy middle layer containing blood and with a decrease in effective conductivity of the skull with age. Also, important is the variability in skull thickness. The 10th–90th percentiles are 2.4–4.6 mm and 3.0–4.9 mm for 1–½ year old girls and boys. That is, the range is 50–60% of the means. At the age of 25, the 10th–90th percentile range is 40–50% of the means for women and men.

EEG signals may be distorted not only by skull defects, but also by the brain-skull and scalp-air boundaries of EEG waveforms in certain circumstances. Goff et al. (1978) have shown that the attenuation of scalp potential is highest for focal cortical sources and lower for extended cortical and subcortical sources. The attenuation of potential may be as much as about 50 times greater for a 6° cortical source compared to a focal source at the center of the brain and as much as about 100 times greater for such a shallow focal source compared to extended sources subtending a solid angle between about 72° and about 180° regardless of depth. This large variation, depending on source depth and extent, implies that the EEG signals on the scalp would be most likely different or deformed in comparison to the signals on the cortex. The components due to focal cortical sources may be small relative to deeper sources and thus some of the cortical components may be difficult to be identified or distinguished, being overshadowed by signals from extended cortical or deeper subcortical sources.

In summary, the MEG system 10 assesses neonatal brain functions and serves as a useful non-invasive clinical tool for monitoring physiological functions of the pre-term and full-term neonates born with possible neurological disorders.

Figure 2B:
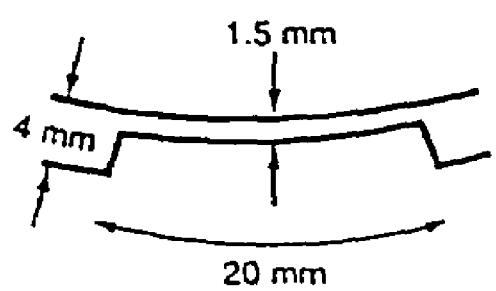
FIG. 2B is a diagram illustrating the wall thickness of a portion of the headrest of the headrest assembly of FIG. 2A.
Figure 3:
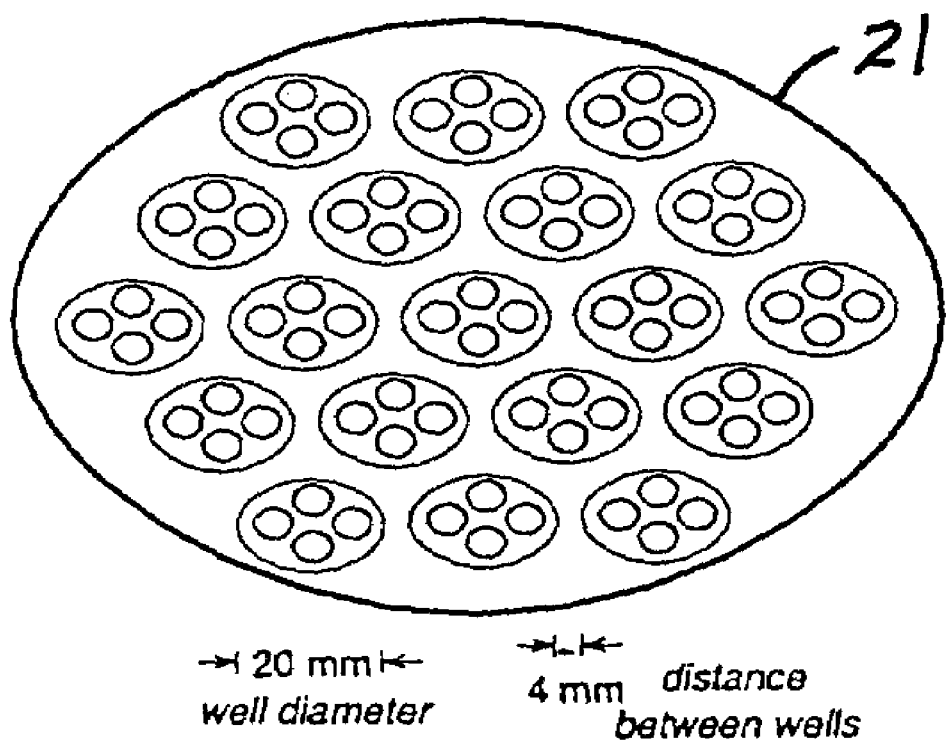
FIG. 3 is a diagrammatic view of the rear surface of the headrest of FIG. 2B and the headrest and illustrates one embodiment of the arrangement of sensor modules of the headrest assembly of FIG. 2.
Figure 4:
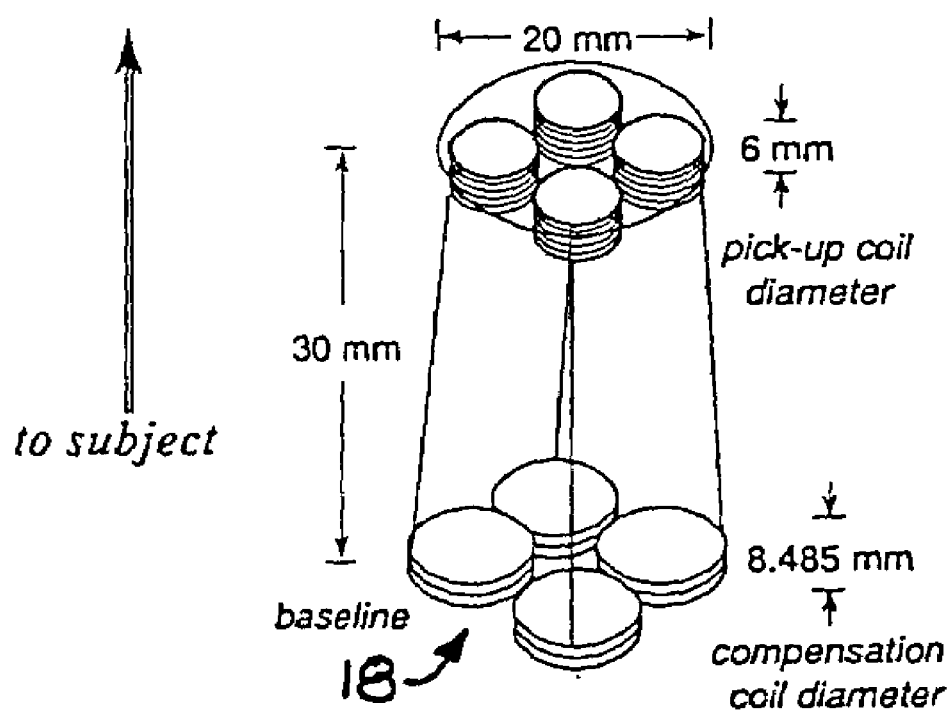
FIG. 4 is a diagram illustrating a single 4-channel sensor module.

FIGS. 2 and 3 show one embodiment of the headrest assembly 16 of a system 10 configured as a contoured semi-ovoid having a honey-comb shaped rear wall. The honey-comb rear wall design enables the placement of the MEG detection sensor coils at a distance of about 1.5 mm or 2 mm (FIG. 2B) from the outer surface of the headrest 21 and, at the same time, provides a sufficient strength to protect the headrest 21 against the vacuum. The space where the sensor detection coils and SQUID dewar are housed may be in vacuum to provide thermal insulation.

The sensor array of sensors 18 in one embodiment of the system 10 consists of 19 clusters of 4 sensors, each arranged as shown in FIG. 3, such that there is a reduced amount or minimum of space between individual sensors 18, given the honeycomb structure. Such modules may be built with a noise level of less than 10 fT/$\sqrt{Hz}$. The preferred embodiment of the headrest uses a honey-comb rear-wall design with individual circular or elliptical windows or recesses (FIG. 3) for the 19 modules, each module (or cluster) including 4 channels of sensing coils. The primary advantage of using individual windows or wells is the ability to achieve close spacing to the head while providing strength to withstand against vacuum. In this regard, the sensors 18 are positioned within the recesses in the rear wall where the headrest wall is the thinnest.

The headrest assembly 16 was tested to determine whether the individual windows or recesses in the honey comb rear wall design can withstand against the vacuum (one atmosphere pressure) of the dewar 27. Extending the theoretical results, the expected deflection was calculated at the center of a G-10 fiberglass window or recess against the differential vacuum pressure of one atmosphere as a function of window or recess diameter and thickness. The deflection was calculated using a Mathcad routine based on Roark's formula for deflection (Roark and Young, 1975). A specific case of flat circular plate with fixed edges and uniformly distributed pressure was exploited. Young's modulus (E) of $2 \times 10^6$ was used for G-10. Table 1 shows the results:

TABLE 1

Theoretical deflection at center of G-10

| Window Diameter (mm) | Window Thickness (mm) | | | |
|---|---|---|---|---|
| | 0.51 | 0.64 | 0.76 | 1.02 |
| 25.4 | 0.25 | 0.13 | 0.08 | — |
| 27.9 | 0.36 | 0.18 | 0.10 | — |
| 29.2 | 0.43 | 0.23 | 0.13 | — |
| 30.5 | 0.51 | 0.25 | 0.15 | 0.08 |

The deflection was less than about 100 μm for a 1.0 mm-thick window with a about 30 mm were chosen to be slightly larger than the diameter needed to accommodate a 20-mm diameter module. These theoretical results were verified empirically. We constructed a 28-mm diameter G-10 window of varying thicknesses, fixed the window on top of a fiberglass cylinder using epoxy seal and then evacuated the inside of the cylinder. The deflection at the center of the window was measured with a micrometer. Table 2 shows the results:

TABLE 2

Measured deflection at center of G-10 window

| Window Diameter (mm) | Window Thickness (mm) | | | | |
|---|---|---|---|---|---|
| | 0.41 | 0.53 | 0.84 | 1.22 | 1.58 |
| 27.9 | 0.68 | 0.25 | 0.13 | 0.08 | 0.03 |

Standard error of mean = 0.01 mm

The empirical results were quite close to the predicted values shown in Table 1. Interpolating from Table 2, the deflection was less than about 100 μm for a 1.0-mm thick window. The vacuum was held by the window even for a 0.4-mm thick window. Based on these results, the honey comb rear wall design with a wall thickness of between about 1.0 mm and about 1.5 mm appears to be safe to use for the system 10.

The safety of the window was evaluated with yet another test. A 25-mm diameter chrome-alloy ball bearing was dropped from varying heights onto the center of selected 28-mm diameter windows. The windows were epoxied onto the vacuum test fixture and a vacuum gauge measured the integrity of the window during impact. Table 3 summarizes the results:

TABLE 3

| Window Material | Thickness (mm) | Drop Height (cm) | No. Drops | Comments |
|---|---|---|---|---|
| G-10 | 1.02 | 20 | 2 | no visible damage |
| | | 40 | 2 | no visible damage |
| | | 60 | 2 | no visible damage |
| | | 100 | 1 | no visible damage |

TABLE 3-continued

| Window Material | Thickness (mm) | Drop Height (cm) | No. Drops | Comments |
|---|---|---|---|---|
| G-10 | 0.84 | 100 | 1 | slight craze, fast leak |
| | | 40 | 2 | no visible damage |
| | | 60 | 10 | no visible damage |
| | | 100 | 5 | slight craze, slow leak |
| G-10 | 0.33 | 20 | 2 | no visible damage |
| | | 40 | 1 | crack through center |

The results of this drop test appears to demonstrate that a G-10 fiberglass window can withstand a significant impact even for a wall thickness of about 1 mm. The 1-mm-thick window did not show any visible damage nor leak even when the large steel ball was dropped from the height of about 60 cm. This second test, thus, reinforces the conclusion that a honey comb design with a wall thickness of between about 1.0 and about 1.5 mm appears to be safe to use for the system 10.

In addition to testing individual windows, the safety of an entire headrest 21 was tested. For the purpose of this safety evaluation, a headrest with a uniform wall thickness was constructed and determined the deflection of the center of the headrest and its ability to withstand against one atmospheric pressure was determined. The baby's head was modeled as an ellipsoidal volume with a radius of curvature of about 6 cm along the coronal section and 8 cm along the sagittal section, using a standard reference for the head sizes (Lusted and Keats, 1978). The negative mold for the headrest was then carefully made with gelucel wood, sealed with polyurethane varnish and then heavy carnuba wax was applied as a mold release prior to applying the fiberglass. Polyester resin and glass cloth were laminated directly into the negative mold. In manufacturing the system 10, a positive mold of the representative baby's head may be made from the negative mold and the headrest may be made from this positive mold to ease removal of the cast form.

Each one of the sensors 18 is a first-order asymmetric, axial superconducting gradiometer. The sensors 18 are arranged in clusters of 4 separated by the honeycomb rear wall of the window or recess (FIG. 3), although the result is substantially equal spacing between sensors. The expected noise level for the gradiometers with a pickup coil diameter of about 6 mm may be about 10 fT/$\sqrt{\text{Hz}}$ or better. Such a module has been fabricated and determined its noise level has been determined.

Figure 5A:
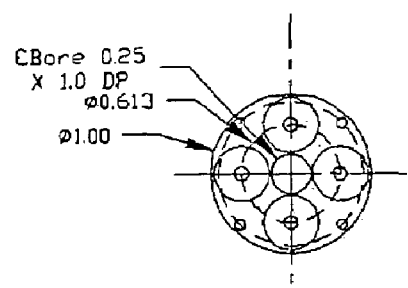
FIGS. 5A, 5B and 5C illustrate one embodiment of a 4-channel module according to the present invention.
Figure 5B:
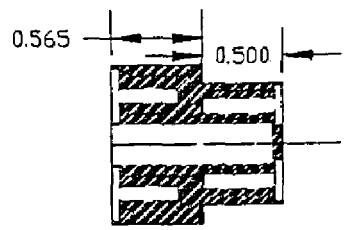
Figure 5C:
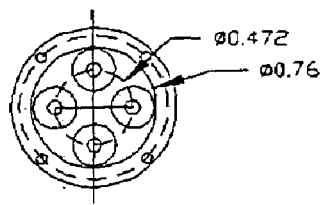

FIG. 5 shows the pickup coils, which are about 6 mm in diameter in one embodiment, since the distance between the pickup coils and the cortical surface will be about 6 mm. This diameter is optimal for this measurement distance in considering spatial resolution and sensitivity.

Figure 6A:
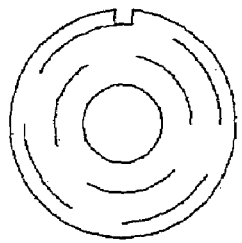
FIGS. 6A, 6B and 6C illustrate a coil form for a pickup coil of the module illustrated in FIGS. 5A, 5B and 5C.
Figure 6B:
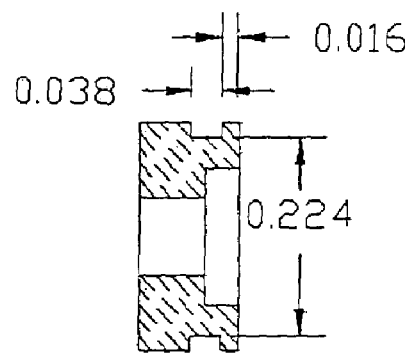
Figure 6C:
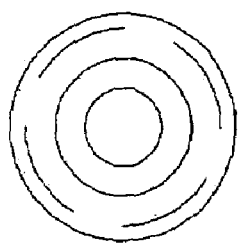

To design a 4-channel module, it may be necessary to calculate the crosstalk between coils for some applications. This was done as a function of coil separation. The calculations demonstrated that the coils in the 4-channel module had to be spaced diagonally by about 12 mm in order to maintain less than about 2% crosstalk. Based on the noise and the crosstalk considerations a 4-channel module was designed, as shown in FIGS. 5 and 6.

Figure 7:
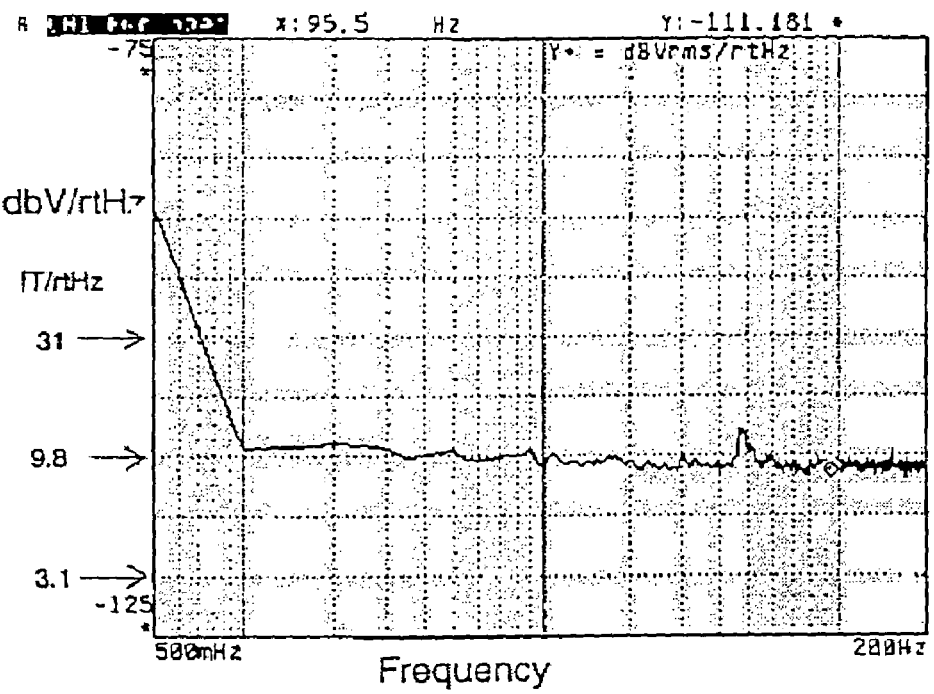
FIGS. 7 and 8 are charts illustrating noise spectra for a 4-channel module with simulated dewar noise.
Figure 8:
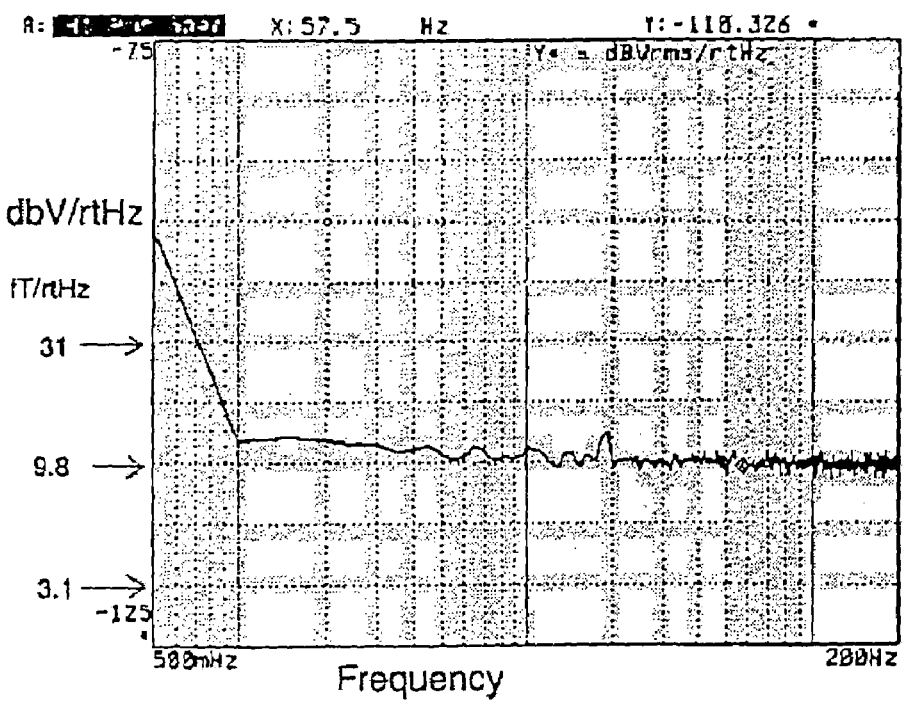

FIGS. 7 and 8 show the noise spectra for the two channels. The noise spectra were quite clean with an elbow frequency (where the 1/f noise starts) of about 1 Hz. Based on these results, it appears that a 4-channel module can be constructed with a noise level of 10 fT/$\sqrt{\text{Hz}}$.

A study of SEFs in human infants using the microSQUID was carried out. The purpose was to show by extrapolation that it should be possible to measure cortical evoked activity without signal averaging using the system 10.

Figure 9:
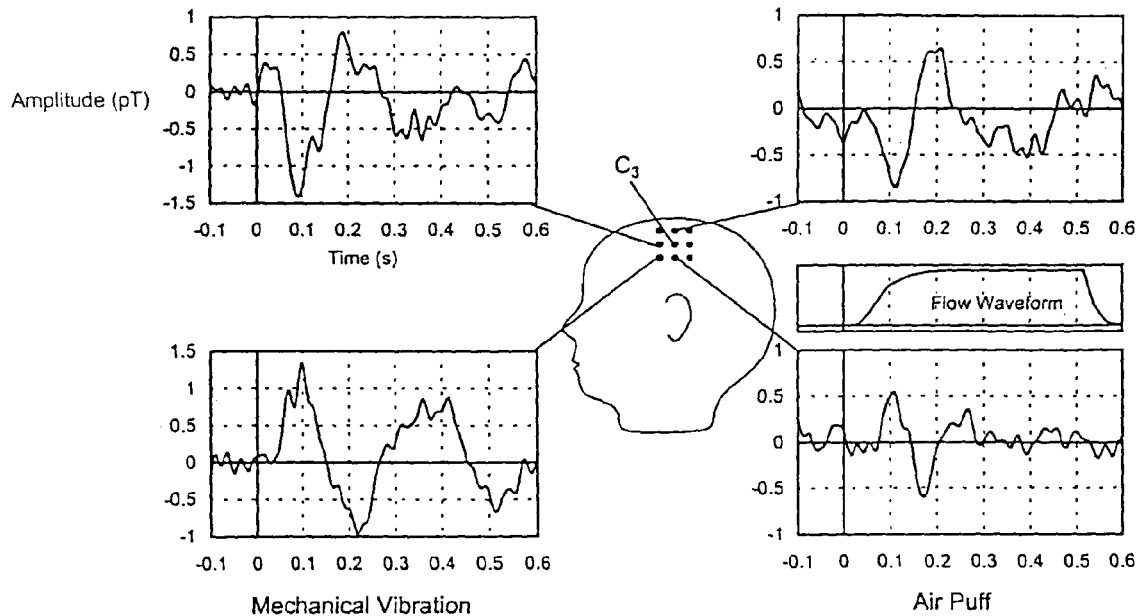
FIG. 9 shows charts representing samples of the somatic evoked magnet fields (SEFs) produced by piezoelectric vibratory stimulations and SEFs produced by air puff stimulations.

FIG. 9 is a graphical representation of the results of the study and show representative samples of the SEFs produced by piezoelectric vibratory stimulations (left) and SEFs produced by air puff stimulations (right). The data with vibratory stimulations were obtained from 9 sessions (9 subjects) and those with airpuffs were obtained from 8 successful sessions (4 subjects). For both stimuli, the SEF reversed its polarity near C3, indicating that its generator was located in the somatosensory cortex below C3. The SEF was stronger for the vibratory stimuli than for the airpuffs, but the waveforms were similar. The initial component was directed into the head over the upper region of the measurement area, whereas it was directed out of the head over the lower part, indicating that the underlying current was directed from the deep layer to the superficial layers of area 3$b$. The latency delay of this initial component for the air puff stimulation relative to the vibratory stimulation is due to the delay in the arrival of the compressed air to the finger via the tubing. The timing of the air puff stimulation, measured with a pressure transducer at the end of the tube, shows a delay of about 35 ms in the start of the pressure and a further delay of about 85 ms before the pressure reached the maximum. The latency delay of the initial component is approximately 35 ms indicating that the initial component was triggered the very early phase of the pressure change.

Figure 10:
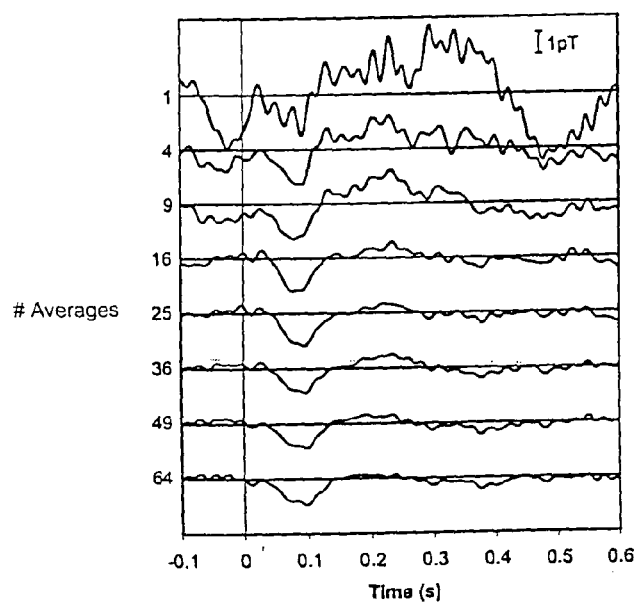
FIG. 10 is a chart showing SEFs that are produced by a vibratory stimulation as a function of number of epochs in the average.

The SEFs obtained as a result of the study strongly support the prediction that similar evoked cortical activity with a comparable signal-to-noise ration (SNR) can be seen in real time using the system 10. The SEFs for airpuffs are averages of 36 epochs, whereas those for vibratory stimulation are averages of 16 epochs. Therefore, it appears that it is possible to obtain SEFs of comparable quality in single trials with the system 10, even for airpuffs, since its noise level is expected to be about 6 times less than that of a conventional microSQUID. In this regard, the SEFs shown in FIG. 10 are produced by a vibratory stimulation as a function of number of epochs in the average. It is clear that reliable SEFs can be seen even after averaging less than 25 epochs, after as little as 4 epochs. The bandwidth of the recordings was 50 Hz, passing between 1 Hz and 50 Hz.

The system 10 enables a study to be carried out by simply placing the baby's head on the headrest assembly 16, instead of placing the detector above the head as was the case for the conventional microSQUID. This inverted design of the dewar 27 of the system 10 provides a sense of safety to the parents who would be present at such a study. Parents would tend to express concern after seeing the baby's head being sandwiched between a conventional detector and the bed. The coverage expected with the 76-channel system 10 tends to speed up the study, since the measurement time is very limited when no sedative is used. The set up time for the measurements is reduced or minimal with the system 10 since no electrodes are required to be placed on the scalp unlike EEG. This also greatly increases the usefulness of the system 10 for routine measurements.

The system 10 may well be very useful for neonatal brain assessment. The results of testing indicate that: (a) an MEG system has little or no affect by the skull (b) EEG is strongly affected by a hole in the skull mimicking the anterior fontanel in the infants, (c) EEG signals are strongly distorted as a function of depth of the active tissue, and (d) the system 10 may well be capable of providing new information about the physiology of the thalamocortical fibers and cortical neurons in certain circumstances.

Figure 11:
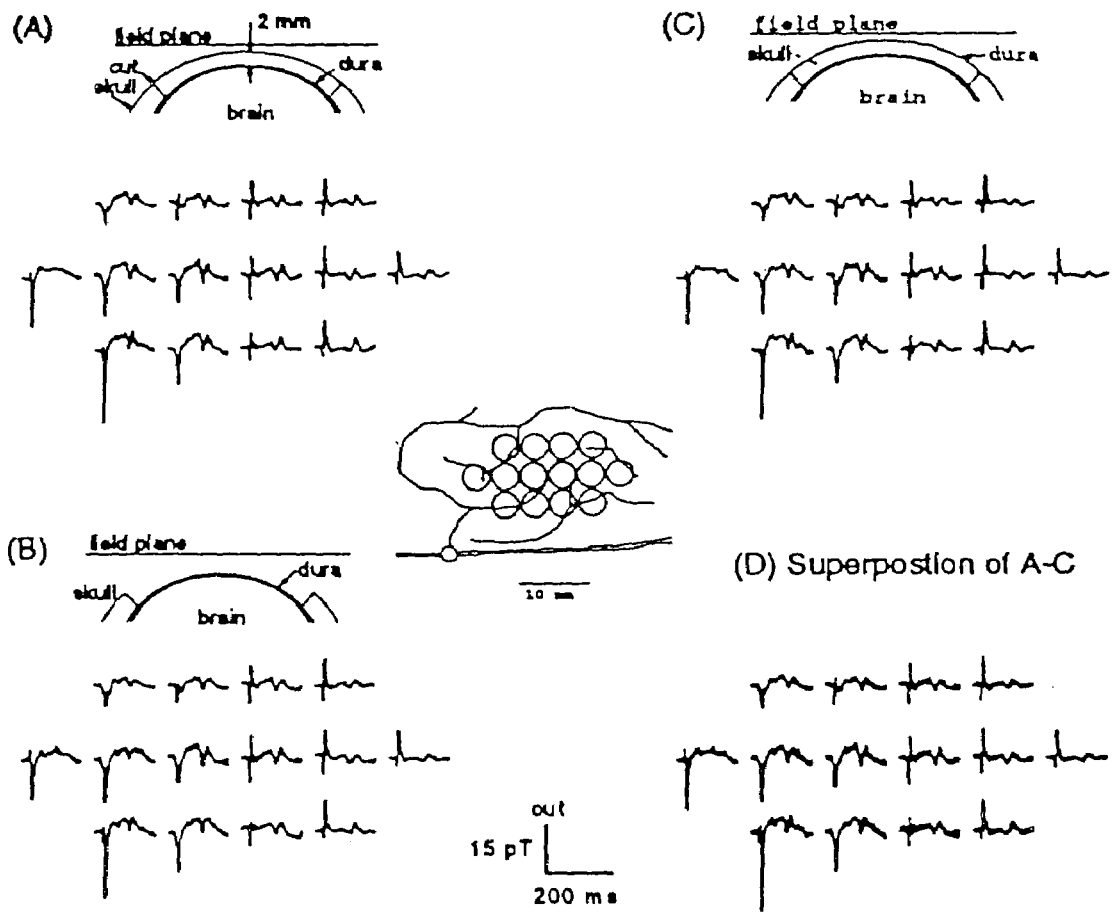
FIG. 11 illustrates charts showing SEFs measured on a plane above the skull of the piglet.

Okada et al. (1999b) have shown that the SEF measured on a plane above the skull of the piglet is virtually the same in waveform and spatial distribution with and without the skull (FIG. 11). The SEFs measured in the skull-on (wave forms A), skull-off (wave forms B), and skull-on again (wave forms C) conditions could be superimposed with no clearly visible differences (wave forms D). Little, if any distortion was seen when the SEF was measured with the skull intact and after the dorsal portion of the skull was removed (Okada et al., 1999a). A quantitative evaluation of the similarity has, however, shown that the skull does influence the external MEG signal as the generator becomes deeper, due to the fact that the skull is not spherical. This result confirmed a theoretical result by Hämäläinen and Sarvas (1989) showing that the MEG signal outside the head calculated with a boundary element model is the same regardless of whether the scalp and skull are present. It also confirms an experimental finding by Barth et al. (1986) showing that a large hole in the skull of a human cadaver does not distort MEG signals produced by an artificial source embedded in the cranium.

Figure 12:
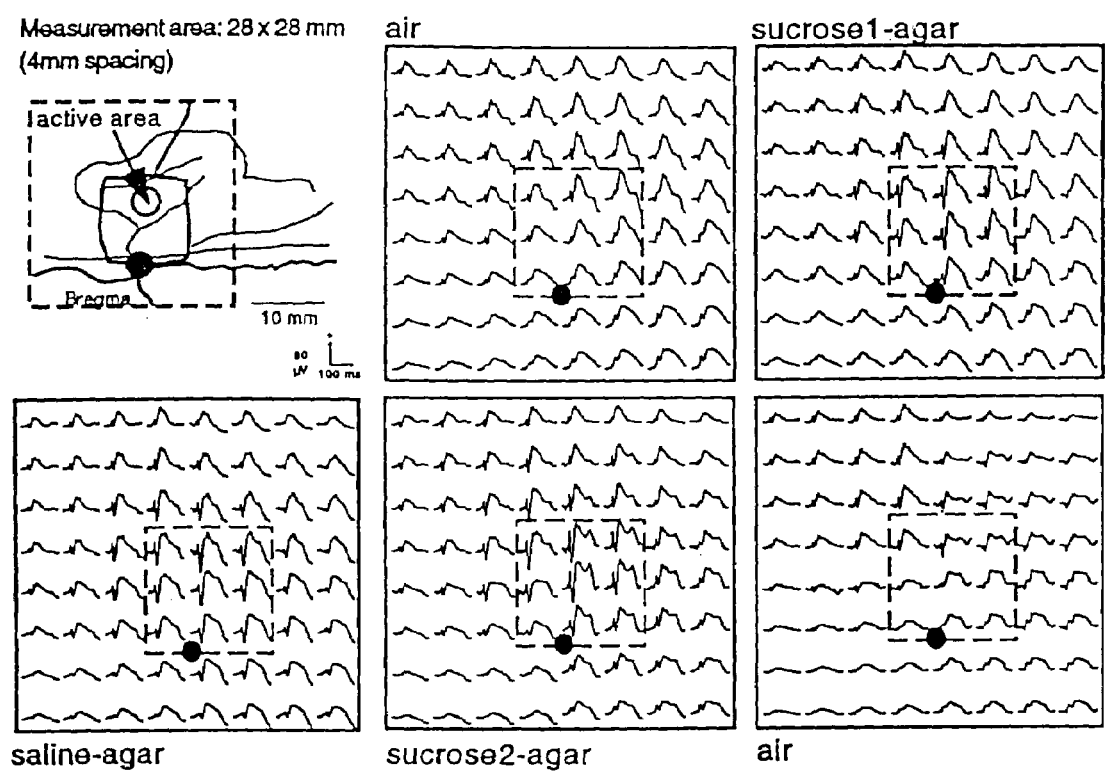
FIG. 12 illustrates charts showing an outline of the somatic evoked potential measurement area on the skull with a square hole over the left hemisphere.

There does not appear to be any study which explicitly demonstrated a distortion in the waveform and spatial pattern of EEG signals caused by a hole such as one mimicking the fontanel in human infants. The large size of cranium in the piglet preparation used in Dr. Okada's laboratory enables one to test this question empirically. FIG. 12 shows an outline (dashed square) of the SEP (somatic evoked potential) measurement area on the skull with a square hole (12 mm×12 mm) over the left hemisphere. The hole was over the cortical area generating the early responses in the primary somatosensory cortex produced by snout stimulation. The SEP was mapped with a 16-channel electrode array placed on a 0.9% NaCl saline-soaked filter paper covering the entire measurement area and mimicking the scalp that was removed. The SEP pattern was measured in three conditions differing widely in the electrical conductivity of the hole, so that the distortion can be measured as a function of conductivity. The hole was filled with air ($\sigma$~=0), isotonic 3% agar containing 330 milliequivalent of sucrose ($\sigma$0.01 S/m close to the conductivity of the skull), with isotonic 3% agar containing 0.9% NaCl ($\sigma$~1.28 S/m). Under these conditions, the SEPs (bandwidth: 1–200 Hz. 60 epochs/ave), especially their early components, were large in sucrose- and saline-agar compared to the air conditions.

The distortion due to conductivity differences in the hole is clearly revealed by the difference map shown in FIG. 13A (each trace bandwidth: 5–200 Hz, 60 epochs/ave). The differences were large between the sucrose and air conditions where the conductivity of the sucrose-agar should be close to the conductivity of, in this case about a 2.5 mm thick, skull. The differences were also quite reproducible as seen by the similarity in the sucrose1-air and sucrose2-air different maps.

The Laplacian transformation is becoming more commonly used in deblurring the scalp EEG pattern (Gevins et al., 1994,1999; Le et al., 1994; Nunez et al., 1994). This method is used to estimate the current emerging or entering the scalp along the direction perpendicular to the surface as a result of neuronal activity in the brain. This current is conventionally estimated by solving the Poisson equation. In practice, the current Im is estimated from a discrete version of this equation: Im □4V(x0,y0)−V(dx,y0)−V(−dx,y0)−V(x0,dy)−V(x0,−dy), when the potential is measured at five positions centered at position x=x0 and y=y0. The Laplacian estimate of currents emerging through the filter paper (mimicking the scalp) is shown for the three conditions in FIG. 13B. The calibration is based on an electrode separation (dx=dy) of 4 mm and a conductivity of 0.016 Siemens/m for the sucrose-agar and 1.27 Siemens/m for the saline-agar. Note that the current magnitudes are much larger over the saline agar. This result clearly demonstrates that currents leak through a hole and distort the EEG pattern on the scalp when such a hole is above an active area of the cortex. In sum, these results empirically demonstrate that EEG signals are distorted by a hole in the skull, suggesting that the skull defects such as the fontanels and sutures may profoundly distort EEG signals in infants.

The following study compared the SEPs measured on the dura and on the scalp and, similarly, the SEFs measured on the dura and scalp in order to determine whether these signals seen outside the scalp are similar to those over the cortex. Goff et al. (1978) showed that the potentials due to focal cortical generators are more attenuated than those due to extended cortical or deeper sources when the potential is measured on the scalp. This implies that the waveform of the SEP on the cortex or dura should be distorted when it is measured on the scalp. The "transparency" of MEG, on the other hand, implies that the SEF on the scalp should be similar in waveform to that on the cortex or dura.

Figure 14:
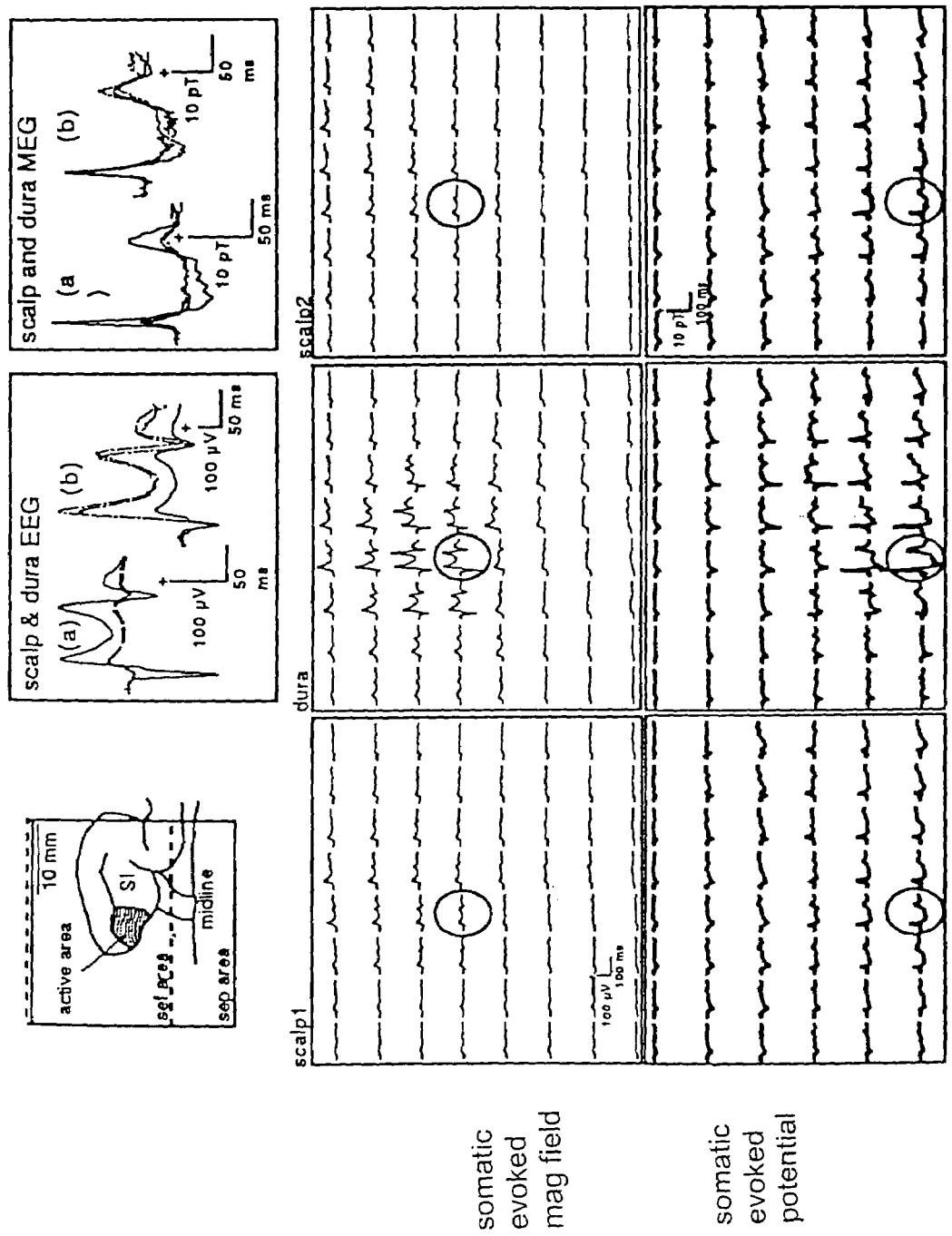
FIG. 14 are charts showing the somatic evoked potentials (SEPS) measured over a square area.

These experiments were carried out on piglets of less than 1 week of age (1–6 days) as a neonatal model of human newborns. The skull of these piglets are 0.5 –1.5 mm in thickness over the dorsal portion of the cranium. The scalp is about 1.5 mm in thickness. They do not possess fontanels, but the sutures are still present and the cranial bones are loosely attached. FIG. 14 shows the SEPs measured over a square area (indicated by the solid line) and the SEFs measured over the dashed area, both roughly centered over the active area in Si responsible for early cortical responses. The snout was electrically stimulated and the SEPs were measured first on the scalp, then with the scalp and skull removed and finally on the scalp again in order to control for possible changes in the physiological condition of the animal. The procedure was repeated for SEF measurements. The scalp and skull were cut before the experiment, then the skull was replaced and the scalp was attached to the intact skin with a suture. The suture was removed for dura measurements and then the scalp was sutured again. The combined thickness of the skull and scalp was 3 mm. It can be seen that the SEP and SEF were very similar in the scalp 1 and scalp 2 conditions, indicating the animal was in stable physiological condition and other extraneous factors did not contaminate the results (signal bandwidth=1–200 Hz, 30 and 60 epochs/ave for SEF and SEP, respectively).

The inset in FIG. 14 labeled "scalp and dura EEG" compares the SEP at its potential extremum for the early cortical component (indicated by an open circle) in the scalp1, dura and scalp2 conditions. The solid curve in (a) is the dura SEP and the two dashed curves are the scalp SEPs. The peak amplitude of the first component of the scalp SEP was magnified to match that of the SEP on the dura as shown in (b). Clearly, the later components of the magnified scalp SEP are larger than the corresponding components of the SEP on the dura, with a good reproducibility for the two scalp conditions. Thus, the attenuation ratios are different for different components of the SEP and thus the scalp SEP is distorted in waveform in comparison with the dura SEP.

The same comparison was made for the SEFs. The SEF distribution on the dura was more compact than the distribution over the scalp due to the shorter measurement distance, just as was the case for the SEPs. Taking this into account, the waveforms were compared at the field extremum of the earliest component of the SEF in the three conditions. The inset in FIG. 14 labeled "scalp and dura MEG" compares the waveforms at the location indicated by a circle in the three conditions. In (a), the scalp SEFs (two dashed curves) were weaker than the dura SEF (solid curve), but they could be scaled by a constant (see b), again by enlarging the scalp SEF to match the peak of its earliest component with that of the dura SEF. Thus, the SEF waveforms were comparable on the dura and scalp. In sum, the results of this study indicate that it may be possible to measure SEF over the scalp as if the scalp and skull were absent, whereas the SEP on the dura may be distorted on the scalp.

The above result implies that it should be possible to non-invasively measure cortical activity with MEG as if the skull and scalp were removed and the sensors are practically placed on the cortex if the skull and scalp are thin as it is the case for neonates and furthermore if the sensors can be placed very close to the scalp. This suggests that it may be possible to non-invasively measure cortical activity as if we had electrocorticographic sensors were positioned on the cortex.

Figure 15:
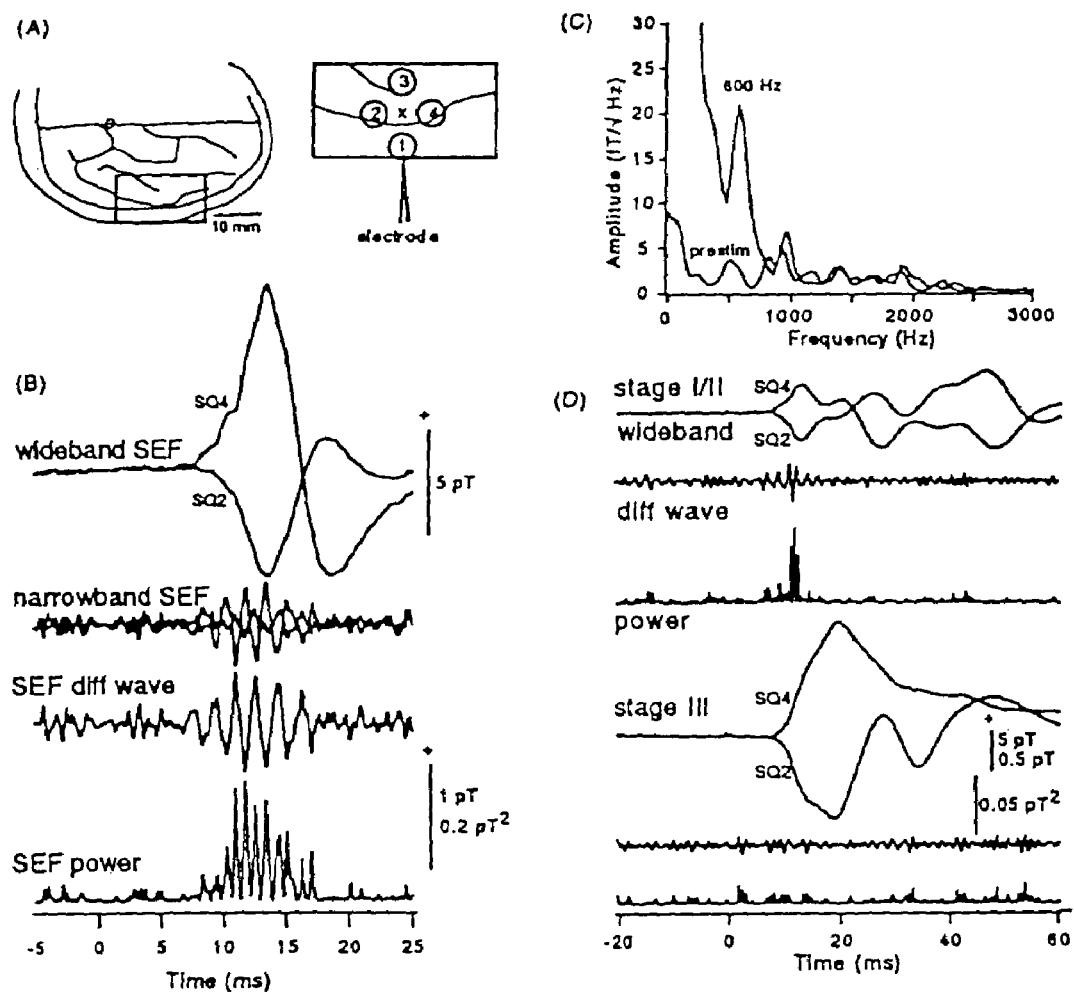
FIGS. 15 illustrates charts showing the outputs from a 600 Hz signal for a piglet.

It has been suggested that the high-frequency signal, the so-called 600 Hz signal, may reveal spike activity (Curio et al., 1994a, b; Hashimoto et al., 1996a; Haueisen et al., 2000a, b). This study has shown that it is possible to detect the 600 Hz signal and determine the origin of this signal in the piglet model using the microSQUID. FIGS. 15A–D show that the 600 Hz signal from the SI of the piglets has properties very similar to those found in the human SEP and SEF. The SEF was first scanned over the SI and then the 4-channel detector was placed directly above the generator of the first cortical response (marked by x in FIG. 15A). In some experiments, the SEP within the cortex was measured simultaneously or sequentially with the SEF in the same animals using a glass micropipette or a 16-channel microelectrode array. In others, SEPs were measured separately. FIG. 15B shows the wideband (1 Hz–3,000 Hz) signal at locations SQ2 and SQ4 along with the narrowband (416–2, 083Hz) SEF, the difference wave between the SEFs measured at SQ2 and SQ4 and the power of the difference wave (square of the difference wave). The amplitude spectrum of the wideband signal (FIG. 15C) was very similar to that found in the humans with a clear peak around 600 Hz (Curio et al., 1994b; Hashimoto et al., 1996a). The SNR of this signal compared to the noise level during the prestimulus period was 10:1. Also in agreement with human results (Emerson et al., 1988; Yamada et al., 1988; Hashimoto, 1996a), the amplitude of the first SEF component corresponding to the human N20m increased while the amplitude of the 600 Hz decreased with an increase in depth of sleep induced by an increase in the level of the anesthetics (ketamine/xylazine) (FIG. 15D).

Signals with the quality shown in FIGS. 15A–D were obtained from the humans with an average over about 1,500–5,000 epochs (Curio et al., 1994b, Hashimoto et al., 1996a). The signals are based on average of 3,000 epochs, even though the measurement distance was about 8 mm in the present study and probably 40 mm in the human studies. If the source strength was the same in the humans and piglets, the signal should be about 25 times ($(40/8)^2$) stronger. The signals in humans are typically 10–30 fT peak-to-peak. In the present study the signal was as much as 400 fT as compared to the expected value of 250–450 fT. Thus, the magnitudes do scale. The test results indicate that the system 10 is 5–6 times more quiet than a conventional microSQUID and thus there is needed about 25 times less average or about 100 epochs to obtain signals of comparable quality in the piglets. This implies that it should be possible to measure this signal from infants by averaging about several hundred signals since the scalp and skull add to the distance of measurement.

Figure 16:
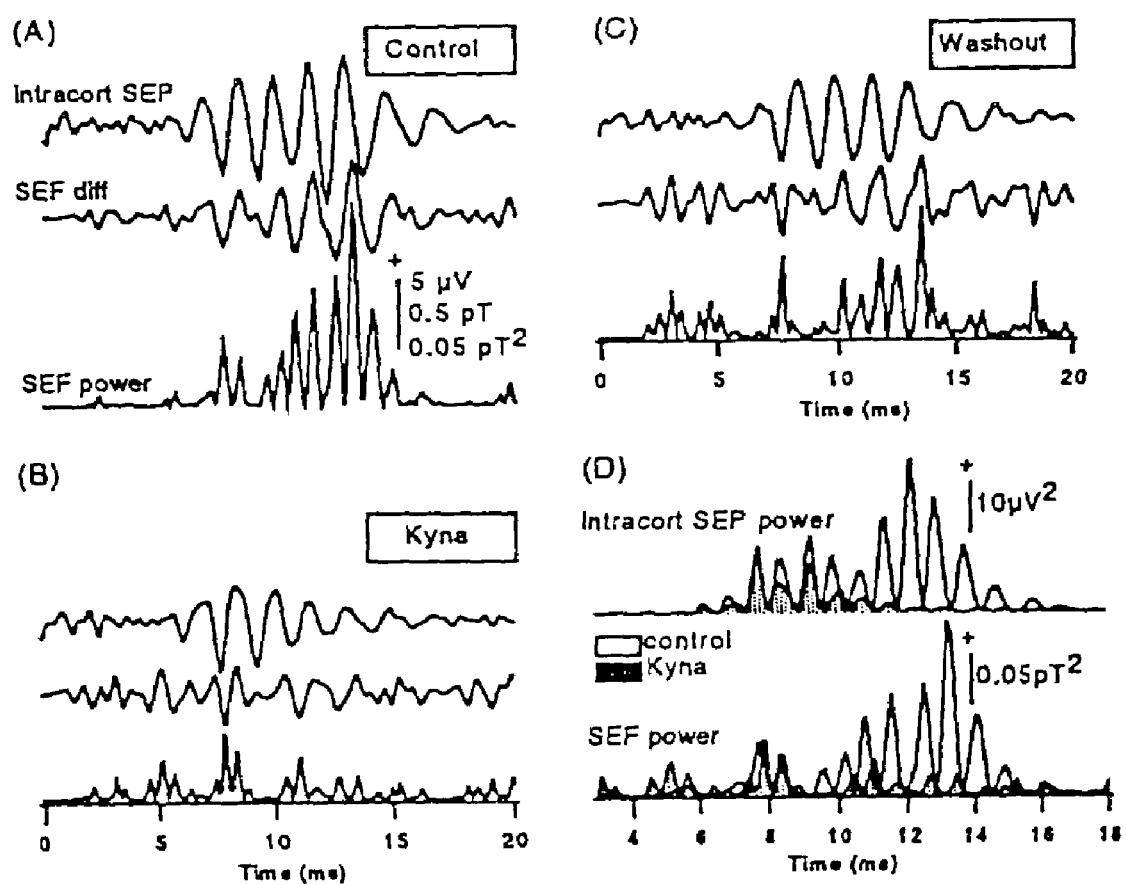
FIGS. 16 illustrates charts showing recordings of SEF outside the brain and intracortical SEP.

Taking advantage of the animal model, the origin of this 600 Hz signal was also determined. Simultaneous recordings of SEF outside the brain and intracortical SEP revealed that the narrowband signals measured with MEG were very similar to the extracellular intracortical activity (FIG. 16A). This indicated that the 600 Hz signal was generated in the cortex. Based on human studies, it has been proposed that the generator of this 600 Hz signal may be the thalamocortical axonal terminals (Gobbele et al., 1998), inhibitory interneurons in the cortex (Hashimoto et al, 1996a; Mackert et al., 2000) or excitatory cortical neurons. Kynurenic acid (Kyna, 20 mM), a non-specific antagonist of excitatory amino acid neurotransmitters, was used to separate the presynaptic and postsynaptic components of the 600 Hz signal. The SEF and intracortical SEP were measured simultaneously with the microSQUID and a 16-channel electrode array fixed in place in the cortex during the control condition without Kyna (FIG. 16A, control). This showed that the SEF power consisted of two components, one around 8 ms and the other between 10–15 ms post-stimulus. Application of Kyna with a pair of glass micropipettes in the projection area of the snout greatly reduced the second component, whereas the first component was intact (FIG. 16B). This second component showed partial recovery during the washout phase (FIG. 16C). FIG. 16D shows the selective effects of Kyna on the first component of the simultaneously measured SEF and SEP. Thus, there are Kyna-insensitive and sensitive components which indicate that there are pre- and postsynaptic contributions to the high-frequency signal.

Figure 17:
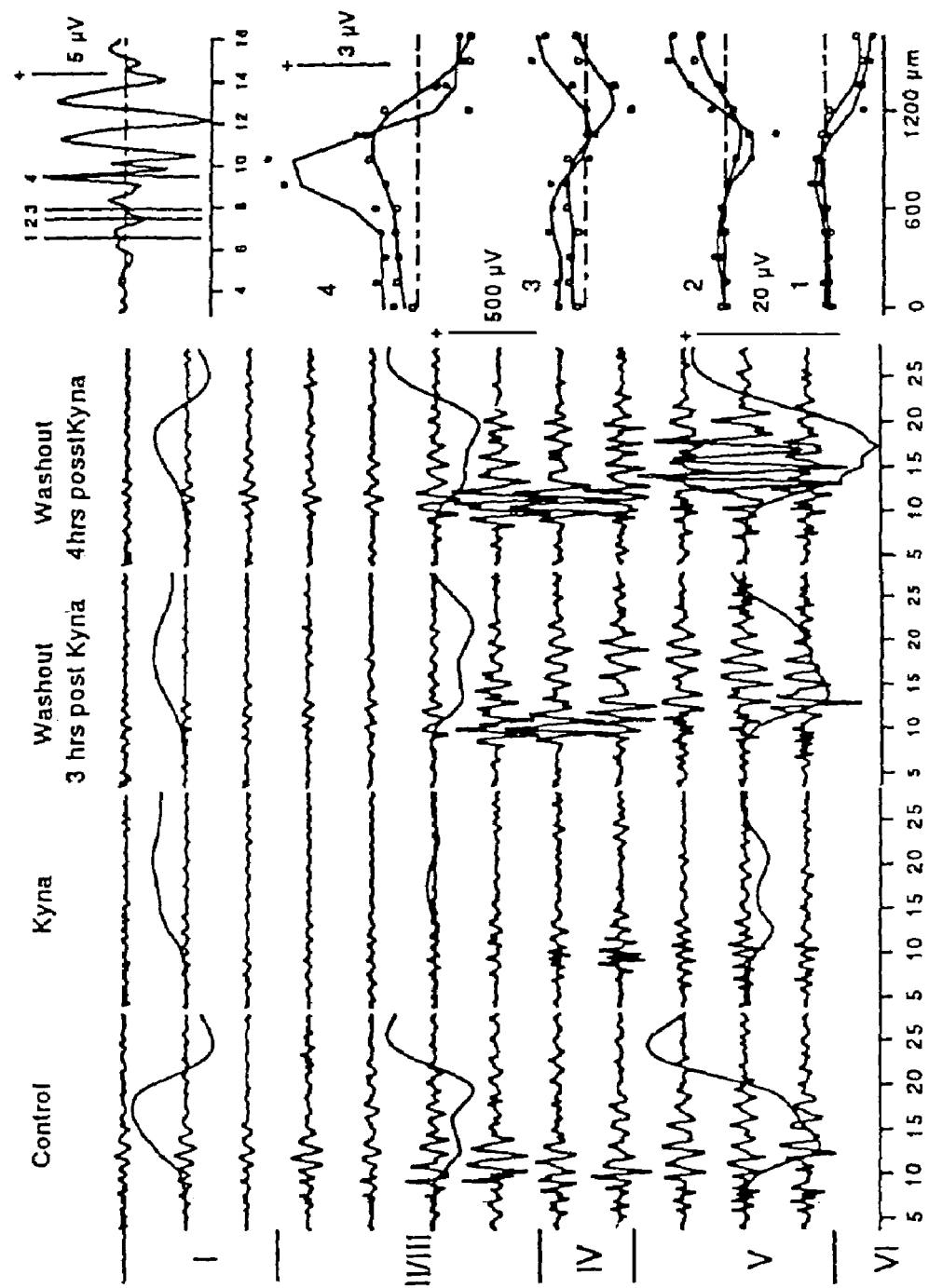
FIG. 17 are charts showing that the Kyna-insensitive component was localized within layer IV and that the presynaptic component was generated by the thalamocortical terminals within the cortex.

FIG. 17, left, shows that the Kyna-insensitive component was localized within layer IV which is the receiving area for specific thalamocortical afferents. A detailed analysis of the presynaptic component, FIG. 17, right, shows that this component was generated by the thalamocortical terminals within the cortex. The laminar profiles within the control and Kyna conditions showed an initial wave, starting about 6 ms post-stimulus, of extracellular negativity that were strongest near the white matter. This wave did not reverse polarity within the cortex. Then, two components (at time points 2 and 3) showing polarity reversal appeared at 7.2–7.9 ms. The extracellular potential was negative in layer IV (~1,000–1,200 μm) and positive in the superficial and deeper layers, indicating that it was generated by the thalamocortical terminals in the receiving layer. A trigeminal brainstem study showed that the snout stimulation produces activity in the trigeminal nuclei with a shortest latency of about 4.5 ms and that the impulses were carried by the fast, myelinated Aβ fibers with a conduction velocity of 32–42 m/sec. This implies that the thalamocortical volley may arrive in the cortex as early as 7.3 ms, taking into account one synaptic delay in the thalamus. Thus, the Kyna-insensitive component at around 8 ms appears to be of thalamocortical origin on this ground as well. About 1.1 ms later, there was a large Kyna-sensitive component in layer III in the control condition. The laminar profile at its peak (time point 4) is shown in FIG. 17. This is the first post-synaptic component produced by the cortex. FIG. 17, left, shows that this post-synaptic component was produced in layers II–VI with a delay between the activity in layer III/IV and layer V/VI. Also, importantly, FIG. 17, left, shows that this post-synaptic component became larger 3–4 hrs after the injection of Kyna, indicating that this component showed hyper-excitability. This suggests that it was generated by excitatory cortical neurons due to partial blocking of inhibitory neurons by Kyna. It has been thought for a long time that the detection of synchronize population spikes would be extremely improbable based on the careful work of Humphrey (1968a, b) who has shown that the antidromically generated action potentials contribute little to the cortical surface record. However, it appears possible from outside the brain to detect axonal spikes from the thalamocortical fibers and synchronized populations spikes produced by cortical neurons using a high-resolution MEG sensor.

The MEG sensors are housed in a cryogenic container called a dewar that stores liquid helium. The dewar consists of two cylindrical containers. The inner container stores a sufficient quantity of liters of liquid helium which is used to maintain the superconducting sensors operating at the critical temperature such as about 4.2° K. The space between the two containers is in vacuum to provide thermal insulation. The inner and outer containers may be made from a special laminated G-10 fiberglass that is constructed to prevent leakage of helium gas into the vacuum space. The dewar may be placed on the floor of the portable cart. In one embodiment, the dewar weight may be about 100 lb and the total bed system may be about 300 lb, so that it should be portable on wheels.

The body of the inner container may be shielded against heat radiation leak using layers of low conductivity material such as aluminum. The shielding may be installed in removable packs to enable ease of construction and rework. The gap from the inside to the outside may be about 2 mm via independent mounts.

The top section of the dewar may be made separately from the bottom cylindrical containers. It may be a G-10 plate with a cylinder epoxied onto the plate. The plate may also accommodate an exhaust hole from the inner cylinder that lets helium vapor escape into the atmosphere. The exhaust hole may be sealed with a removal thermal shield to prevent heat from leaking into the inner container. The cylinder may be machined so that the headrest can be epoxied onto the cut surface. The headrest may have a curvature that may accommodate the head of infants. As mentioned above the headrest may be ellipsoidal or semi-ovoid with the radii of curvature of about 6 and about 8 cm. This dimension should be sufficient to accommodate infants of up to about two years of age (Lusted and Keats, 1978) for some applications.

Figure 18:
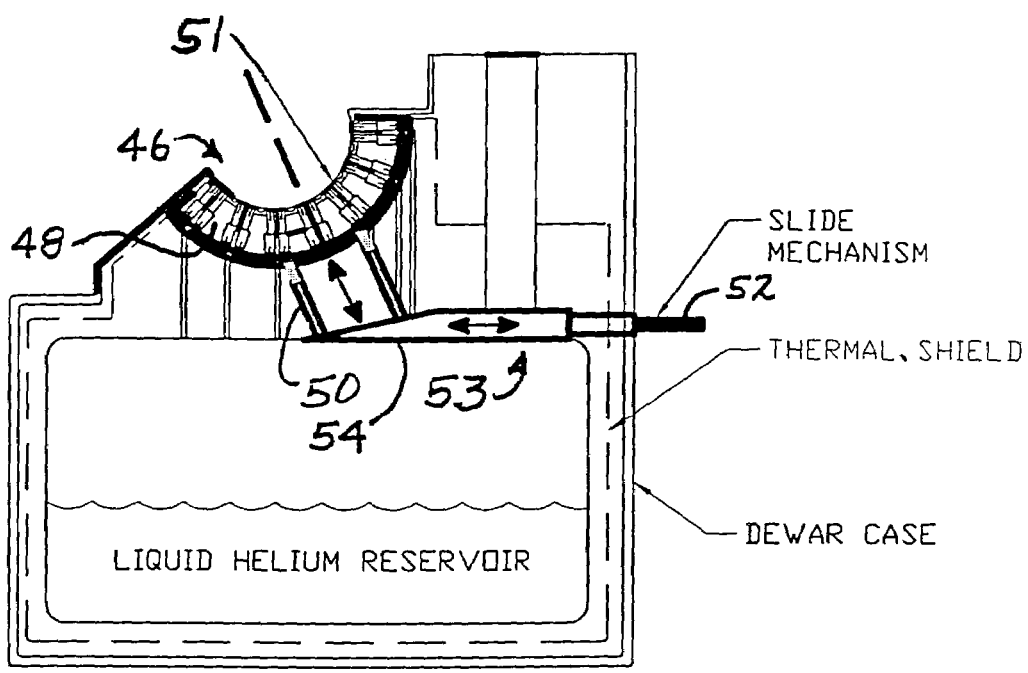
FIG. 18 is a cross-sectional side view of a headrest according to one embodiment of the invention.

As shown in FIG. 1, the sensor pick up coils may be mounted at the top and the associated dc-SQUIDs may be mounted at the bottom of the inner container of the dewar 27. This sensor assembly may be maintained at the superconducting temperature by a cold heat sink attached to the bottom of the inner container. In accordance with another embodiment as shown in FIG. 18, an MEG system 44 have a headrest assembly 46 enables the sensor array 48 to be moved adjustably relative to headrest 51. An actuating mechanism 53 may be installed that may enable an operator to adjust the height of the sensor as array 48 relative to the headrest 51 so that the pickup coils may be as close to the inner surface of the headrest as possible. This may be about 2.0 mm spacing between the outer surface of the headrest and the pickup coils when the system 10 is in use, but about 1 cm below the closest position when it is not in use in order to conserve liquid helium.

The boil off rate for the system 44 is about 4 liters/day when it is not in use and 8 liters/day when in use according to one embodiment of the invention. Assuming the system 44 to be used 12 hours/day, a sufficient size dewar such as a 25-liter dewar may be able to hold liquid helium for 4 days. Thus, helium transfers may need to be made twice a week for some applications.

The actuating mechanism 53 may be made as illustrated in FIG. 18. The shafts such as a shaft 50 supporting the sensor array may be spring loaded and moved up and down by a wedge 54 that may be moved horizontally by a thermally shielded rod 52 that may protrude from the side of the dewar.

Reverting again to the system 10 of FIG. 1, the array consists of 19 modules of 4 channels each for the disclosed embodiment. Each module may be attached to an ellipsoidal support as shown in FIG. 3. The distance between the center of a module to the center of an adjacent module is approximately 24 mm for this embodiment.

Each module consists of 4 channels of first-order, asymmetric, axial gradiometers in the preferred embodiment. However, other numbers of gradiometers may be employed. The most suitable pick up coil configuration is a 12 turn, 6 mm-diameter pick up coil and a 6 turn (spaced by 1 mm), 8.49 mm-diameter cancellation coil. This is desirable for the 3 $\mu\Phi_0/\sqrt{Hz}$ SQUIDS by Quantum Design, San Diego, Calif., or the SQUIDs made by Jena SQUIDs, Jena, Germany. This has a noise level of 2 $\mu\Phi_0/\sqrt{Hz}$ rather than 3 $\mu\Phi_0/\sqrt{Hz}$ with a inductance of 0.6 $\mu$H rather than 1.8 $\mu$H. Thus, the ideal noise (without the noise from the superinsulation and fiberglass wall) should be reduced from 7 fT/$\sqrt{Hz}$ to 4.7 fT/$\sqrt{Hz}$. Furthermore, the number of turns in the gradiometer assembly can be reduced for some applications, thereby making the fabrication of the gradiometers coils relatively easier.

The pickup coils within and across the clusters of 4 are densely packed to increase the spatial resolution. The coil-to-coil diagonal distance within each module is about 12 mm for some applications. The coil-to-coil distance across the modules between the closed coils is about 10 mm. This separation is about three times less than the separation between channels of the latest high-density 200–300 channel whole-head MEG systems made by the CTF Systems and 4D-Neuroimaging.

As the system 10 is designed to operate in an unshielded environment, special precautions may be taken to provide adequate RF shielding. All cryocables (from room temperature to the SQUID sensors) may be RF shielded. The leads from the pick up coils may be shielded using superconducting lead tubes. The dewar superinsulation provides partial RF shielding for the pick up coils. Each module may be RF shielded by wrapping it with a superinsulation material.

An electronic rack may be placed in the body of the portable cart 14 below the mattress or bed 29 (see FIG. 1). This rack houses 84 channels of SQUID control units, 76 channels for the detection coils plus three magnetometers and five first-order gradiometers to be used as reference channels for noise cancellation. All control units may fit into one 19-inch rack-mounted card cage, sufficiently small for the entire rack to fit comfortably within the body of the cart. The dc-SQUIDs may be connected via RF-shielded coaxial cables to the control units.

The SQUID electronics may be powered completely by a suitable dc power supply that may be located close to the AC power outlet of the hospital room. The use of the dc power reduces the line frequency noise that would be sensed by the MEG detection coils.

Figure 19:
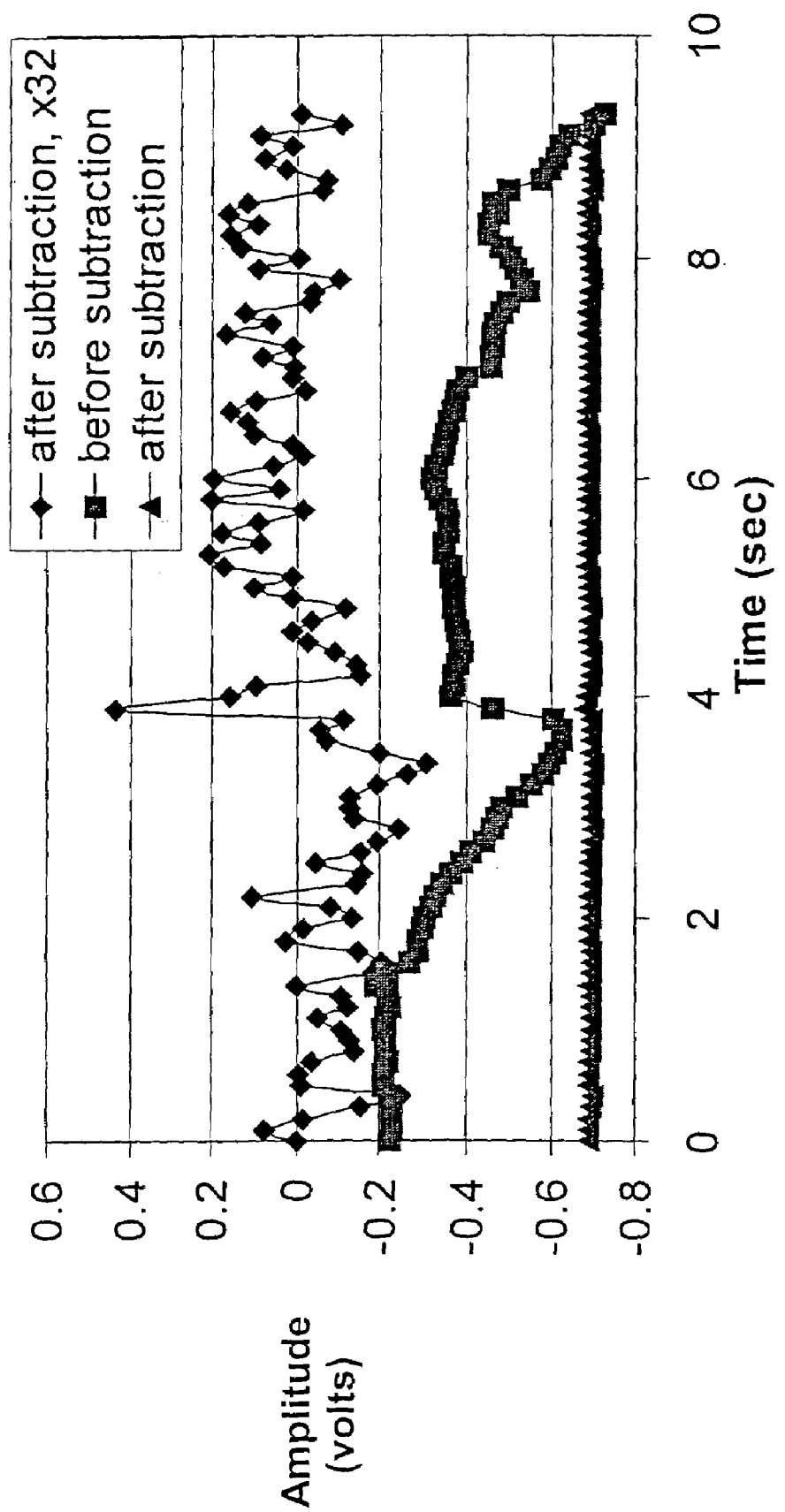
FIG. 19 is a chart illustrating the cancellation of the ambient earth magnetic field changes achieved in the frequency range below about 5 Hz.
Figure 20:
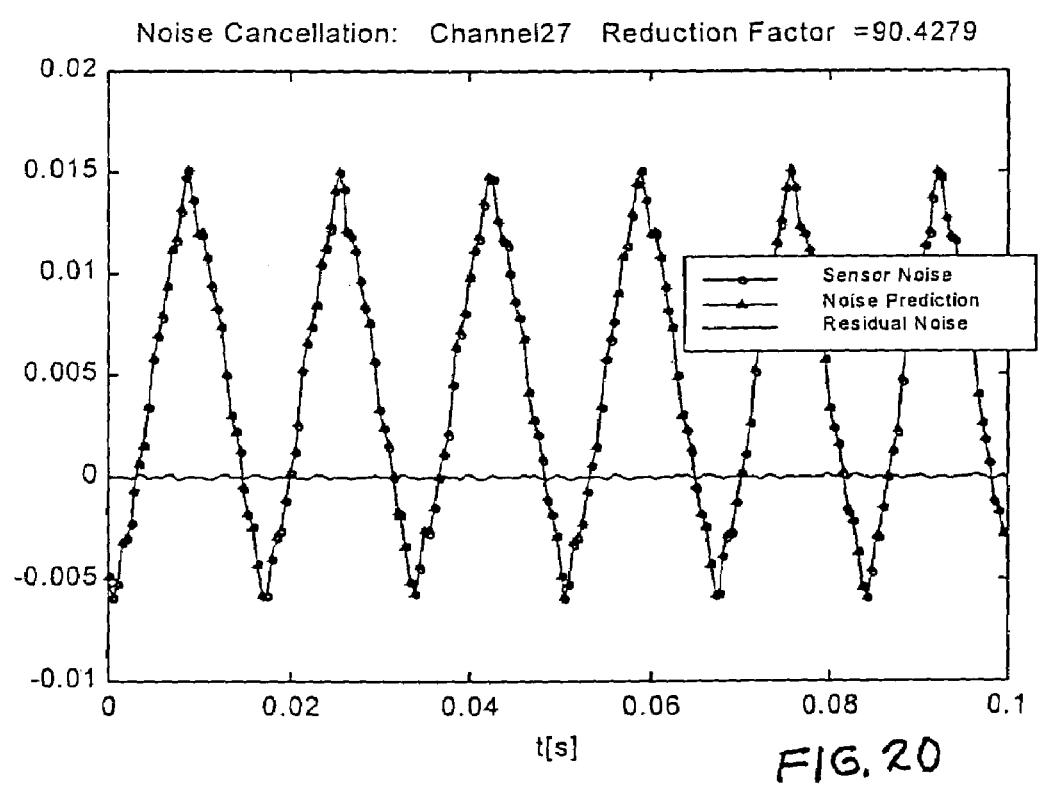
FIG. 20 is a chart showing the noise cancellation for the line frequency noise using 8 reference channels.
Figure 21:
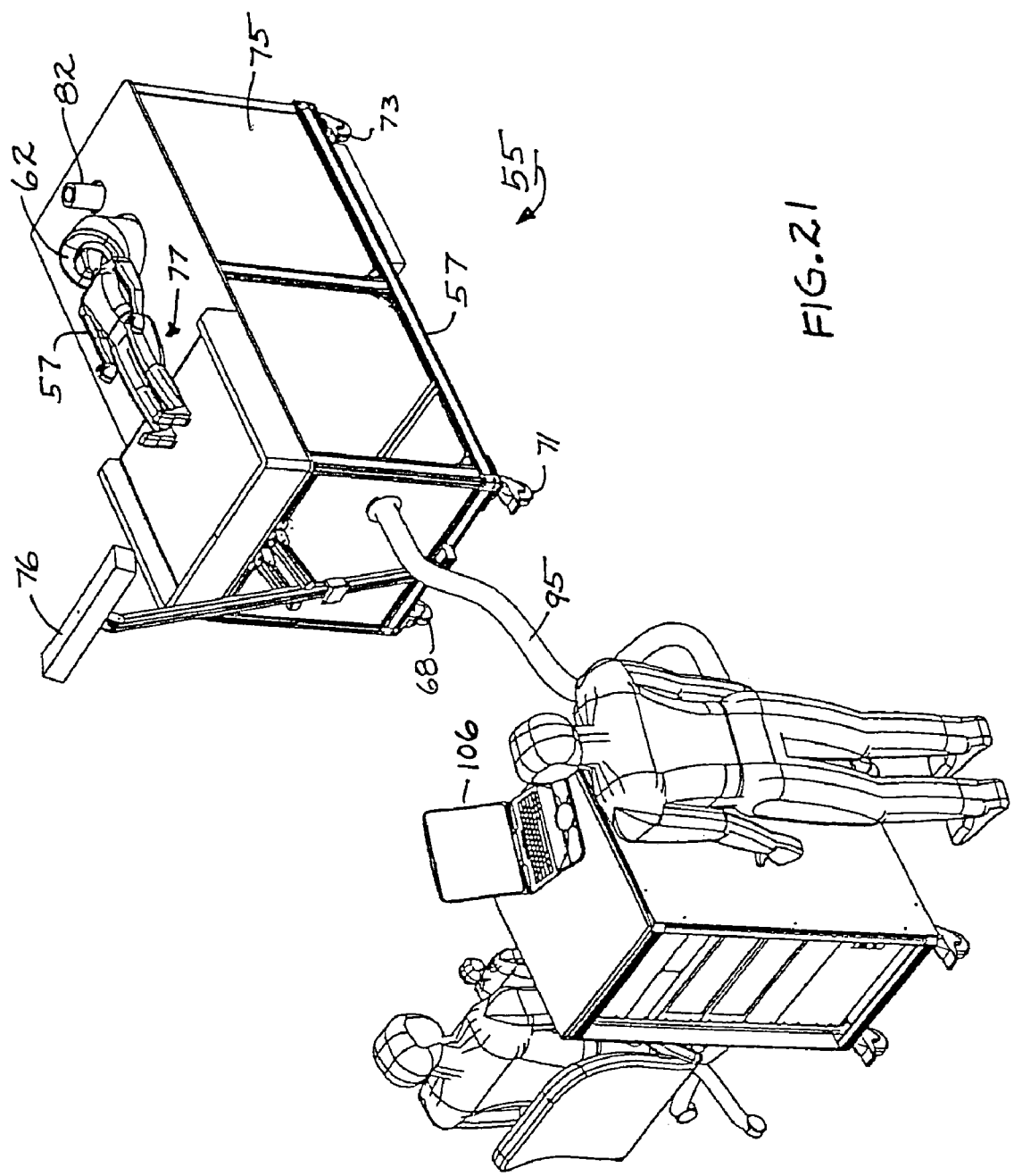
FIG. 21 is a pictorial view of another embodiment of an MEG system, which is constructed in accordance with certain embodiments of the present invention.

The system 10 must operate in electromagnetically unshielded environments such as almost any room in a hospital. Shielded rooms are expensive, costing in some cases between about $500K and $1M, depending on the size and level of magnetic shielding desired. It also makes the MEG systems non-portable. This lack of portability has inhibited a wide-spread use of MEG systems. The system 10 is portable and is capable of operating in many or most clinical settings, in almost any room in a clinic without electromagnetic shielding. In unshielded environments, there may be three types of noise: (1) low frequency magnetic field changes due to the variation in the earth's magnetic field, due to movements of cars, trains, etc., (2) line frequency noise and (3) RF noise. Considering noise problems plus an additional problem of sampling requirement, a new SQUID control unit manufactured by the Systemtechnik Ludwig (STL), GmbH, Konstanz, Germany is currently preferred. The initial stage of noise cancellation is accomplished by using first-order gradiometers which can reject uniform magnetic fields with a rejection ratio of at least about 100:1. The second stage may be accomplished by software cancellation, after recording the data. FIG. 19 illustrates the cancellation of the ambient earth magnetic field changes that have been achieved in the frequency range below about 5 Hz. The data in square symbols ("before subtraction") illustrate the noise level sensed by a second-order gradiometer of liver iron biosusceptometer installed in Torino, Italy. The reference channel in this case was a fluxgate magnetometer. The curve in triangles ("after subtraction") shows the same curve with the same scale after the cancellation. The curve in diamonds ("after subtraction, ×32") shows the noise-cancelled curve after magnifying it by a factor of 32 which corresponds to the ratio of the standard deviations of the signals before and after the noise cancellation. The cancellation by a factor of about 30 achieved in our preliminary work is comparable to the shielding factor of the commercially available two-layer magnetically shielded rooms in the frequency range below 1 Hz FIG. 20 shows the noise cancellation for the line frequency noise using the 8 reference channels. Noise cancellation was performed on data from a 29 channel gradiometer sensor array installed at the Vanderbilt University with an additional eight channels of reference. The eight channels of reference consisted of five gradiometer channels and three magnetometer channels comprising a complete field and field gradient measurement. The test noise data was acquired at a 2 kHz sample rate for one minute with no signal present. The noise was dominated by 60 Hz line noise and its harmonics. A multivariate, linear, least-squares fit was applied to the first 30 sec of the data to determine a linear functional dependence of the signal array channels on the reference channels. The 29 by 8 matrix of fit coefficients was then applied to each time step in the second thirty seconds of the test data. This generated a prediction of the noise in the sensor array channels that was then subtracted from the actual noise measured. Over the 29 channels, it appears that a noise cancellation may be achieved under certain circumstances of up to 90. This noise cancellation scheme may be refined by finding the weights that may be time dependent. This refinement may provide a line frequency cancellation by a factor of greater than about 100.

The data acquisition may be carried out by a PCI-based system that may be attached to the cart 14 as shown in FIG. 1. The outputs from the 84 SQUID control units may be fed to a set of data routers via fiber optic cables. This reduces the rf noise feeding back into the SQUID control unit and into the SQUIDs. The control units are housed in units of three. The fiber optic outputs from four units (12 channels) may be fed at a rate of 480 kByte/sec to a level 1 router. Four of the level 1 routers are fed to the next router at a rate of 1.92 MB/sec. Since there are 84 channels, 7 level 1 routers may be required for some applications feeding to two level 2 routers. The two outputs of the level 2 routers may be fed into a PCI card with a transfer rate of 8 MB/s. This data acquisition system continuously acquires 4-byte data at 10 kHz from 84 channels. A 1 GHz PCI-based PC may be is sufficient for some applications. The STL system may work with the Windows NT.

In some applications, such as in the studies aimed at measuring the 600 Hz activity from the cortex, it is necessary to use a signal bandwidth of 3 kHz for some applications. Thus, the data may be sampled at a rate of at least 8 kHz. The data acquisition may be controlled by software. It provides a complete control over all electronic features. An optical technique may be used to determine the head shape of the infant. This method uses one digital camera to take the pictures of a grid pattern projected onto the baby's head. The distortions of the grid pattern seen by the camera are used to reconstruct the 3D shape of the head and face. This method may be selected since it is completely remote in operation, non-invasive, fast and economical. The image can be obtained in less than 1 second and the reconstruction can be done offline, so that there is no need to worry about movement of the baby's head.

The conventional optical positioning system 28 from Eyetronics may be employed. The accuracy better than 1 mm can be achieved. A conventional lithographic technique is used to prepare the grid pattern. Only a single picture, taken from a slightly different angle than the projection angle, may be sufficient to extract 3D shape information. The input parameters are the relative positions of the camera and the miniature slide projector that may project a single grid pattern onto the face and head, and the deformed grid on the object. To obtain a full 3D model of the head, several overlapping pictures may be taken from different angles. A software, provided by Eyetronics, may be used to integrate the separate images. This process can be completed before the EEG/MEG measurements start.

It may be important for some applications to be able to continuously monitor the position and orientation of the baby's head in order to maximize or at least increase the time available for useful measurements. In studies involving normal, healthy babies, the presently preferred procedure involves no sedative. This means that the study may be done while the baby is asleep. The duration of sleep is typically between about 10 min and about 40 min. Monitoring the head position continuously during this period enables the data to be analyzed during the motion-free periods. The useful measurement period may also be extended due to the monitoring, to the period of wakefulness. Oftentimes the baby keeps his/her head stationary for more than about 10 sec at a time during the transition to the sleep state. Thus, it would be possible to measure the brain activity during the awake stage if the baby's head can be continuously monitored.

There are also other techniques available for both 3D head shape mapping and head position tracking. For the head position tracking there are optical, electromagnetic and laser tracking systems. It may be desirable for some applications to continuously monitor the head with an absolute positional accuracy of about 1 mm during measurements.

Optical Tracking

Optical tracking systems include two or more cameras of known locations. They track three or more marks in 3D. The marks can be either passive (for example, reflective tape) or active (for example, infrared LED's). Optical systems have 0.3–0.4 mm accuracy in a tracking volume of about 1 m$^3$. The update rate is in the 20–70 Hz range. Optical tracking does not tend to interfere with MEG measurements, so that the object location can be synchronized with magnetic measurements.

Laser Tracking

Laser tracking system has the same advantage as optical systems in that it does not tend to interfere with magnetic measurements, and the object position can be synchronized with the MEG data. These systems include a cost effective LaserBird system from Ascension Technology. The accuracy is about 1 mm at about 1 m distance. The tracking is done by scanning the work area with a laser beam. The sensors attached to a baby's head pick up the laser beam. From these data signals the information on the object position is derived.

Electromagnetic Tracking

Electromagnetic tracking systems are widely used with SQUID biomagnetic measurements (for example, EM tracking systems from Polhemus). An electromagnetic transmitter is rigidly attached relative to the pick up coils, and three receivers are attached to the head. The accuracy of this system is on the order of about 1 mm.

Cluster Sensor Shielded MEG System

Referring now to FIGS. 21 through 29, there is shown a high-resolution magnetoencephalography (MEG) system 55 for evaluating neurological impairments of preterm and term babies, for example. The system 55 is generally similar to the system 10, except that the system 55 employs clustered sensors instead of modular sensors, and has other features such as being shielded in a particular manner.

The system 55 is adapted to serve as a non-invasive neurodiagnostic tool in assessing possible neurological dysfunctions and brain development in neonates such as a patient 57. System 55 includes a cart 59 having a headrest assembly 62 disposed in an upwardly facing direction for receiving the head of the patient 57. The headrest assembly 62 is generally similar to the headrest assembly 16, and includes a sensor array generally indicated at 64 mounted below a concave headrest 66 similar to the headrest 21, and as shown in FIG. 55. The cart 59 is designed to be portable and roll along the ground on a set of wheels such as the wheels 68, 71 and 73.

A SQUID dewar 75 is mounted on the cart 57, and includes an optical positioning system 76, which is similar to the optical positioning system 28 of FIG. 1, for the purpose of determining the position of the head of the patient 57. A bed or cushion 77 on the upper surface of the cart 57 permits the patient 57 to lie in a reclined position with his or her head supported from below by the headrest 62.

Figure 22:
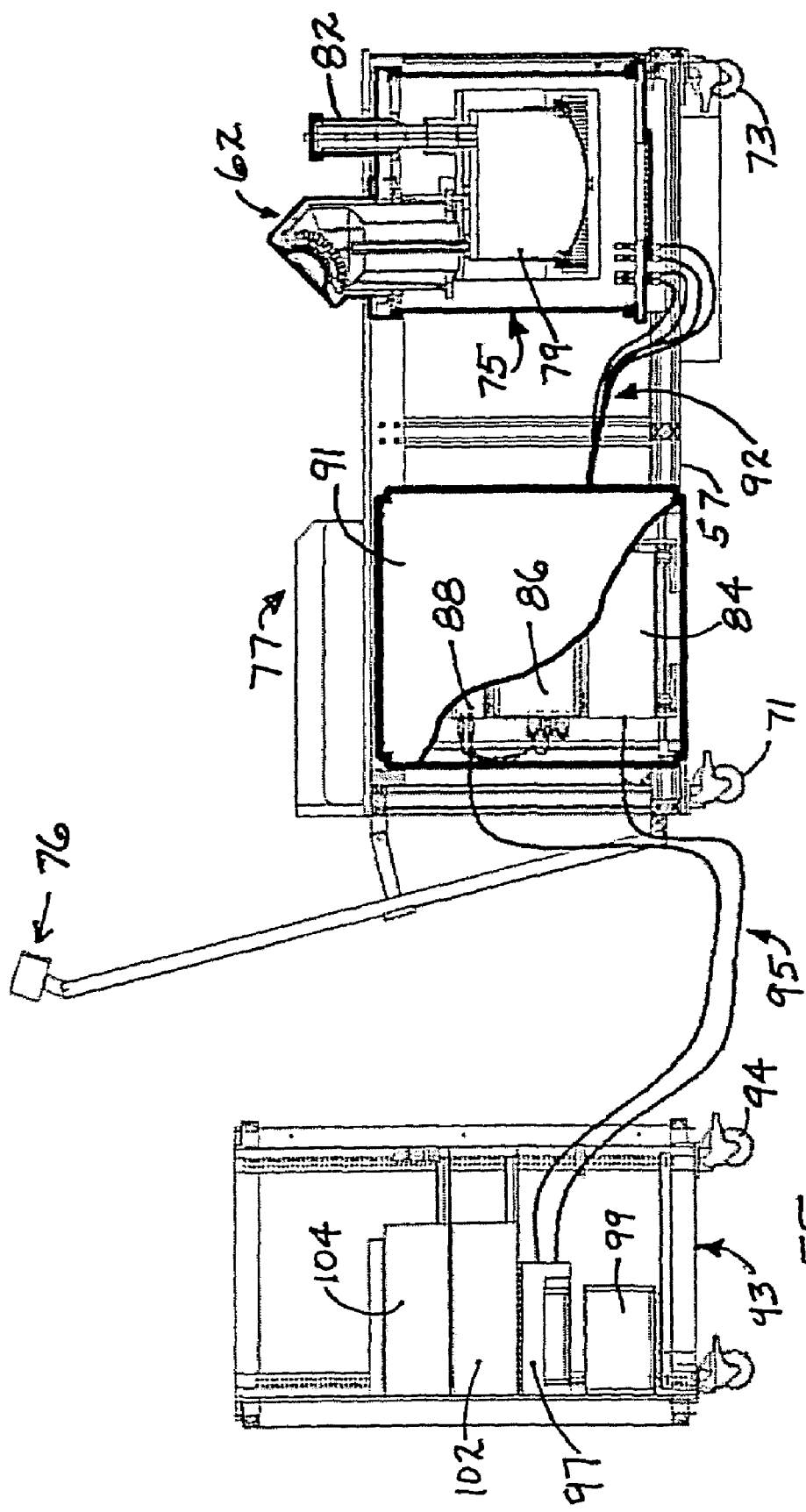
FIG. 22 is a side elevational view of the system of FIG. 21, illustrating it with portions thereof partially broken away for illustration purposes.
Figure 23:
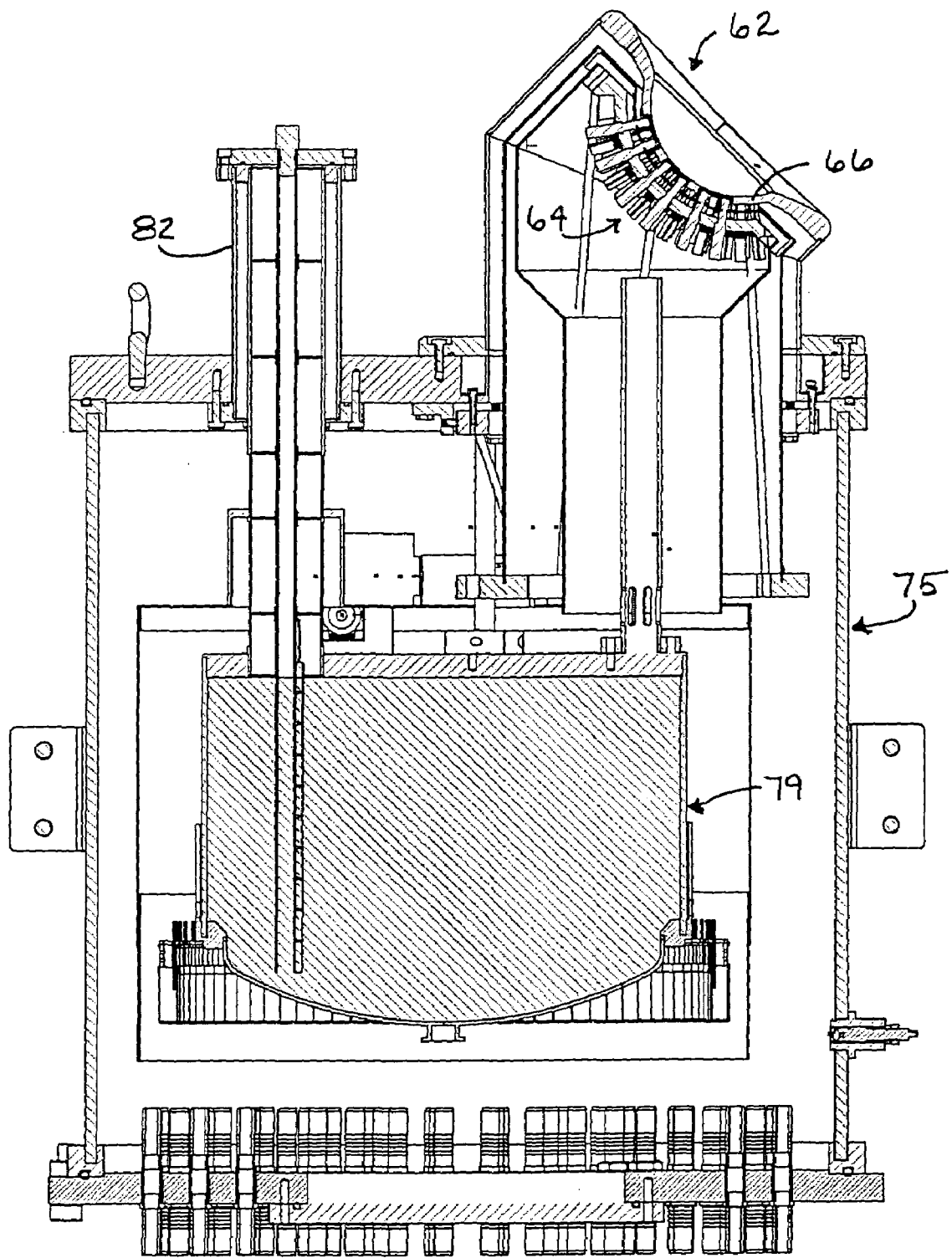
FIG. 23 is an enlarged-scale sectional view of the system of FIG. 21, illustrating the headrest assembly and dewar.

As best seen in FIG. 22, a liquid helium reservoir 79 of the SQUID dewar 75 is a fill port 82 extending above the upper surface of the cart 57. SQUID data acquisition electronic equipment 84 and SQUID phase lock loop electronic equipment 86 are mounted on the cart 57, together with a power hub 88. These electronic components are mounted within a shielded container 91 to protect them against radio frequency interference. The electronic components are connected to the SQUID via a group of cables generally indicated at 92.

A portable trailer 93 is mounted rollably above the ground by means of a series of wheels such as the wheel 94. A group of shielded cables generally indicated at 95 provide power and data channels for the electronic equipment mounted on the cart 57. In this manner, when the cart 57 is moved to the desired location, the trailer including a DC power supply 97 and a transformer 99 can be moved along with the cart 57. A pair of personal computers 102 and 104 are mounted [on] the trailer 93 and communicate with a notebook computer 106 mounted on top of the trailer 93 to be utilized by an attendant.

Figure 24:
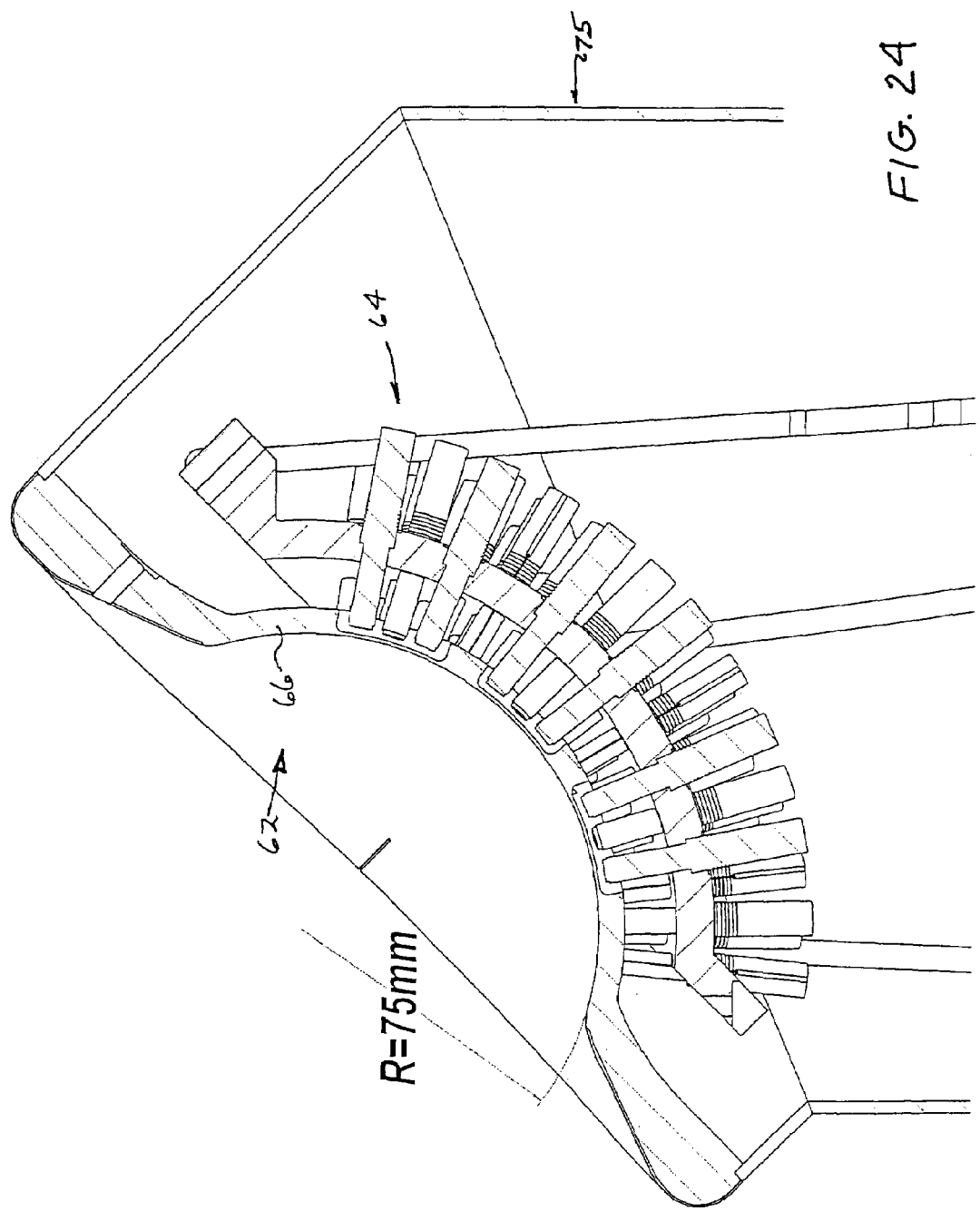
FIG. 24 is an enlarged side elevational sectional view of the headrest assembly of the system of FIG. 21.
Figure 25:
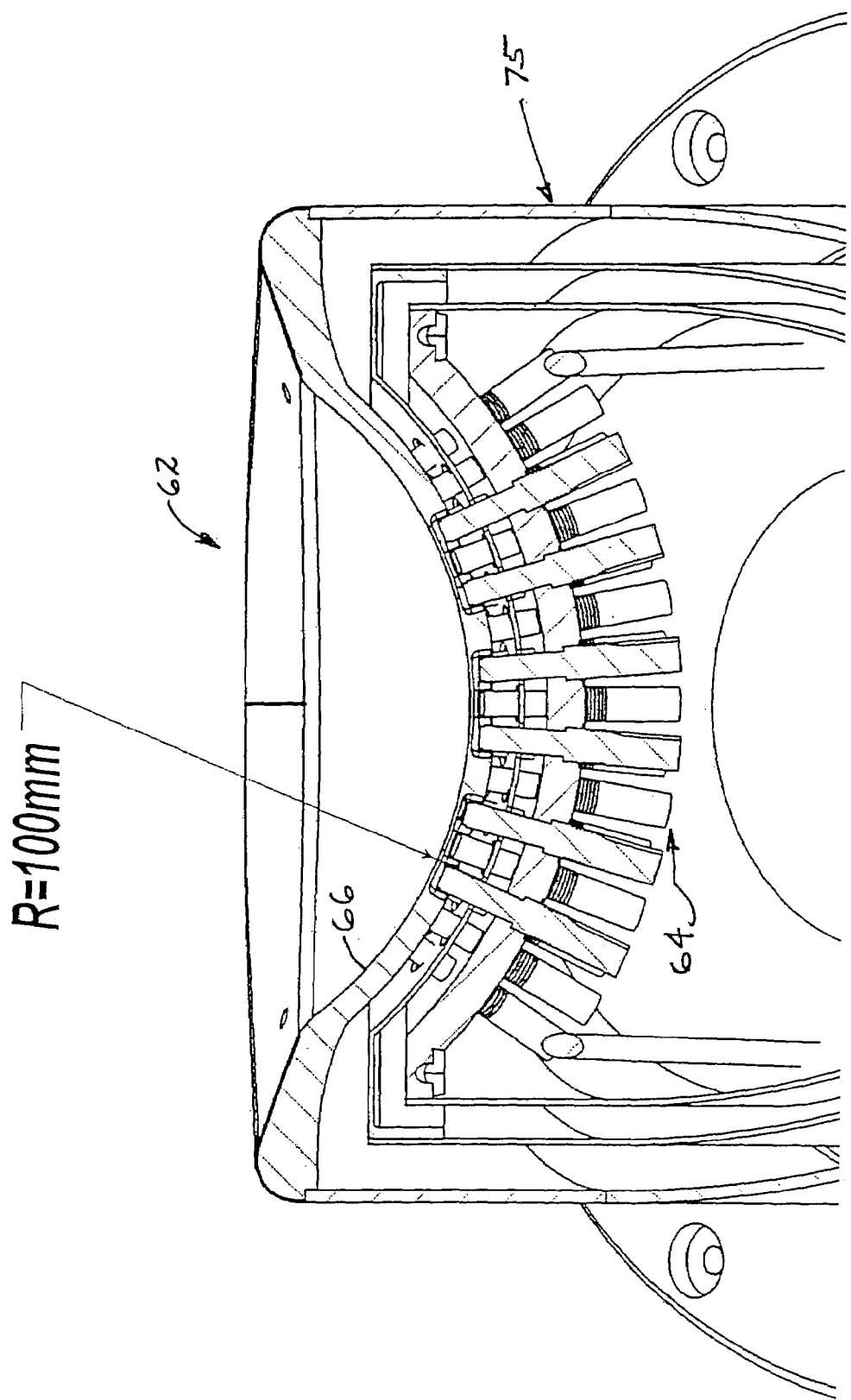
FIG. 25 is an enlarged sectional view of the headrest assembly of the system of FIG. 21, similar to FIG. 24 except taken at a different sectional plane.

The headrest assembly 62 has two curvatures for coronal and sagittal (axial) coverage. As indicated in FIGS. 24 and 25, the headrest assembly 62 is concave and is configured in an ellipsoid shape having a sagittal radius of curvature of between about 80 mm and about 120 mm for the sagittal axis of the head and having a coronal radius of curvature of between about 60 mm and about 90 mm at the coronal axis of the head. A more preferred range of the sagittal radius is between about 90 mm and about 110 mm, and a more preferred range of the coronal radius is between about 70 mm and about 80 mm. Currently, the most preferred sagittal radius is about 100 mm, and currently the most preferred coronal radius is about 75 mm.

The headrest 66 is composed of non-metallic head-insulating structurally strong material. This material is currently preferred to be fiberglass G 10.

Each one of the sensors 64 is a superconducting gradiometer having a pick-up coil diameter of between about 4 mm and about 8 mm. More preferably, the pick-up coil diameter is between about 5 mm and about 7 mm. Currently, the most preferred pick-up diameter is about 6 mm.

The gradiometer sensors are uniformly distributed relatively to the head engageable surface of the headrest 66. Each one of the sensor pick-up coils being spaced apart by a spacing distance of between about 6 mm and about 14 mm. This spacing distance is more preferably between about 8 mm and about 12 mm. As currently contemplated, the sensors are arranged in groups of four, wherein the spacing distance between adjacent sensors of a group is about 8.5 mm and the spacing distance between diagonally disposed sensors of a group is about 12 mm.

Figure 26:
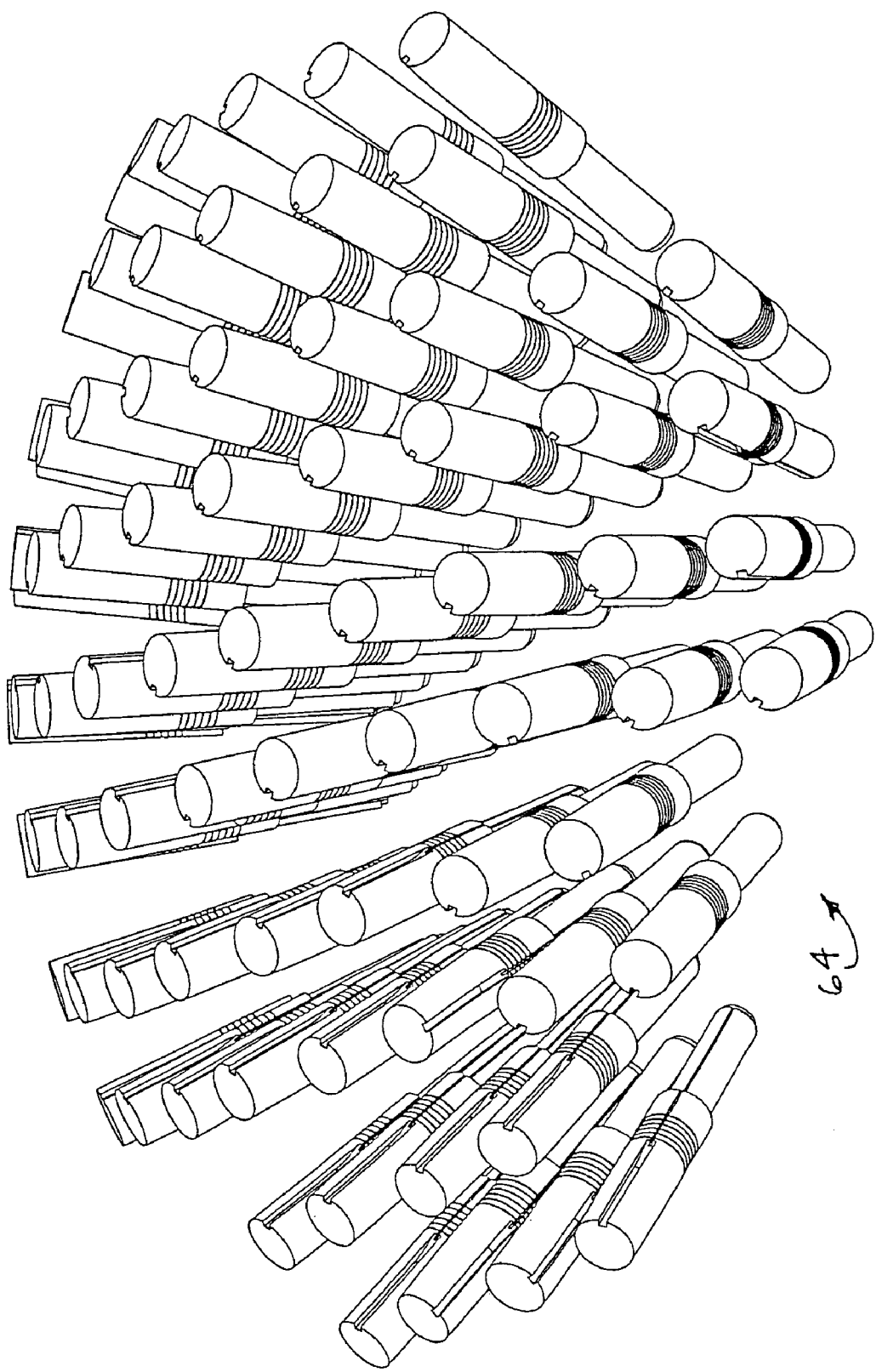
FIG. 26 is an enlarged-scale pictorial view of the array of sensors of the headrest assembly of the system of FIG. 21, illustrating the sensors in their relative positions.
Figure 27:
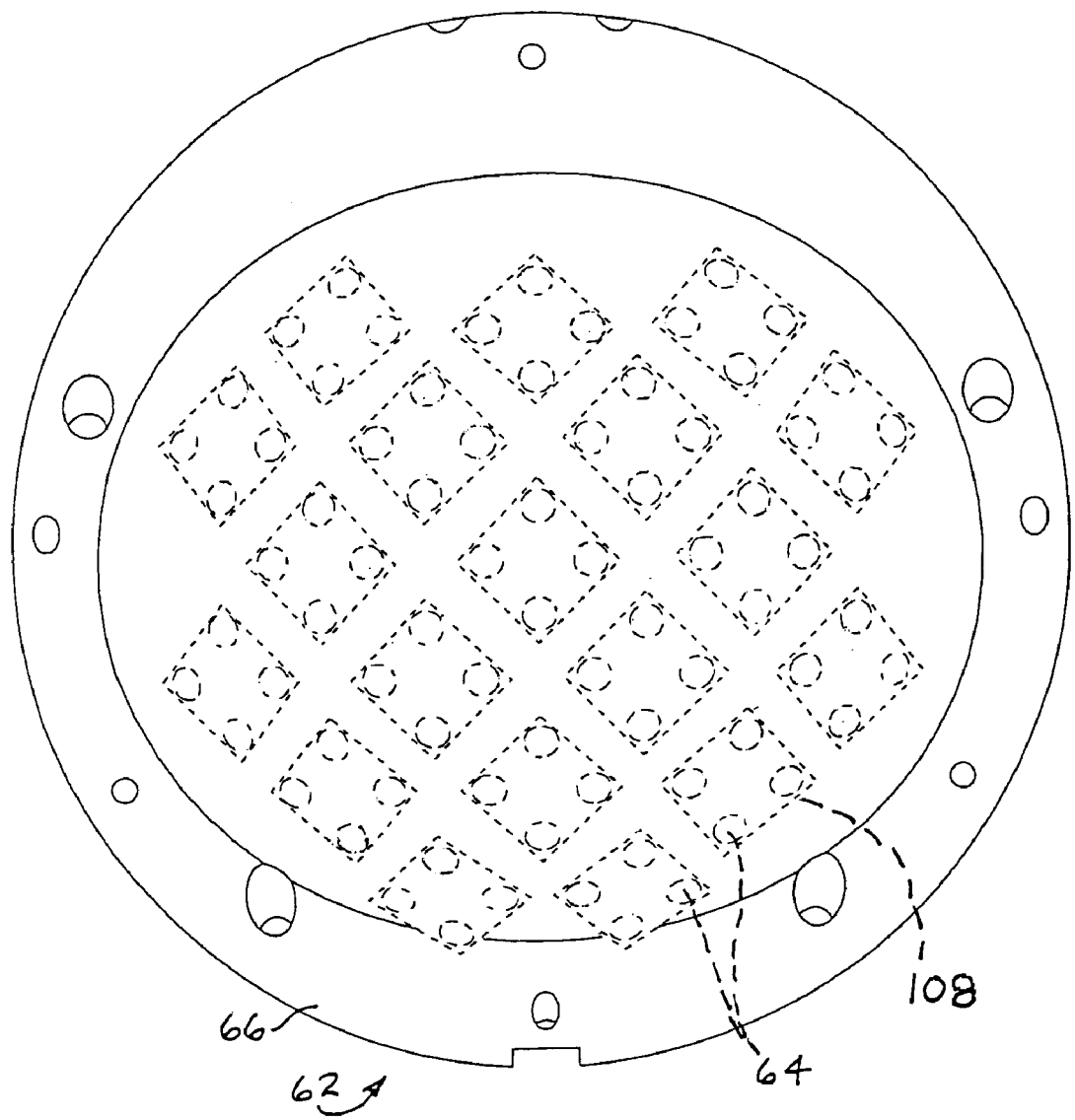
FIG. 27 is an enlarged face view of the headrest assembly of the system of FIG. 21.
Figure 28:
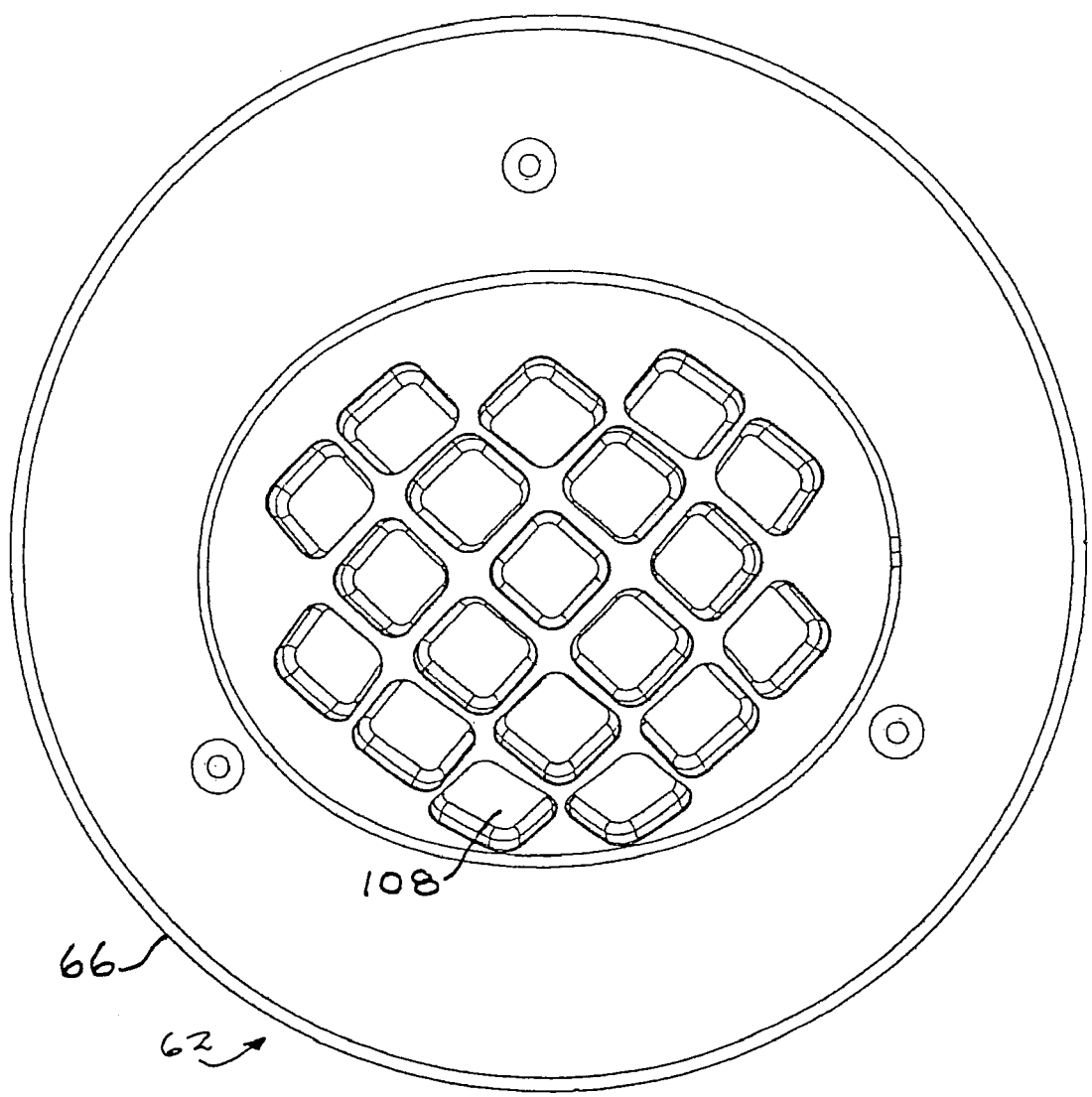
FIG. 28 is an enlarged face view of the rear surface of the headrest assembly of FIG. 27.

Referring now to FIGS. 26, 27 and 28, the sensors 64 are arranged in groups, and the headrest 66 has a corresponding series of windows or recesses such as a recess 108 in the rear surface of the headrest 66 positioned opposite to one of the groups of the sensors. In this regard, each one of the recesses is generally rectangular in shape and is dimensioned to the approximate size of its group of sensors. In this regard, the rear surface of the headrest is arranged in a honeycomb configuration to provide a thin wall construction for the sensors so that the sensors may be positioned in a close relationship to the head of the patient 57. The honeycomb configuration of the rear wall of the headrest 66 is best seen in FIG. 28.

While the sensors 64 are arranged in clusters of four, it is to be understood that there could be other numbers of such sensors clustered together. Also, it is contemplated that each separate sensor may have its own recess or window and not be clustered with other sensors. In the currently preferred example, the sensors are arranged in groups of four, and each one of the four sensors of a group provides a separate communication channel. The channel is usable individually, or in combination or subtracted from one another. Thus, the channels can be summed in various combinations for signal averaging purposes, albeit with a decrease in spatial resolution. Additionally, the differences between channels can be taken, such as by electronic subtraction of their respective voltages to effectively measure planar gradients.

Furthermore, the channels can be subtracted, or used individually.

The dewar 75 is radio frequency interference shielded by multiple techniques. The external portions (those at room temperature) of the dewar is shielded by the application of a thin coating or coatings of conductive material. The product of the coating conductivity and thicknesses is such to provide an eddy current shield with a roll-off frequency of less than 500 kHz. The coating may be applied through various methods including (but not limited to), flame spraying or the use of a metallic enclosure, as well as others. The interior portion of the dewar 75 is also shielded by the use of one or more ultra-thin assemblies of conductive material, such as aluminum. The thickness or thicknesses of the assemblies are such that they act as an eddy current shield with a typical roll-off frequency of less than 500 kHz, but do not significantly attenuate magnetic signals of interest (typically less than 10 kHz).

Additionally, the power cables DC power supply carts or trailer are filtered to prevent radio frequency interference from entering either the electronics or the magnetometer detection sensor coils in the dewar.

Headrest Constant Sensor Gap

Figure 29:
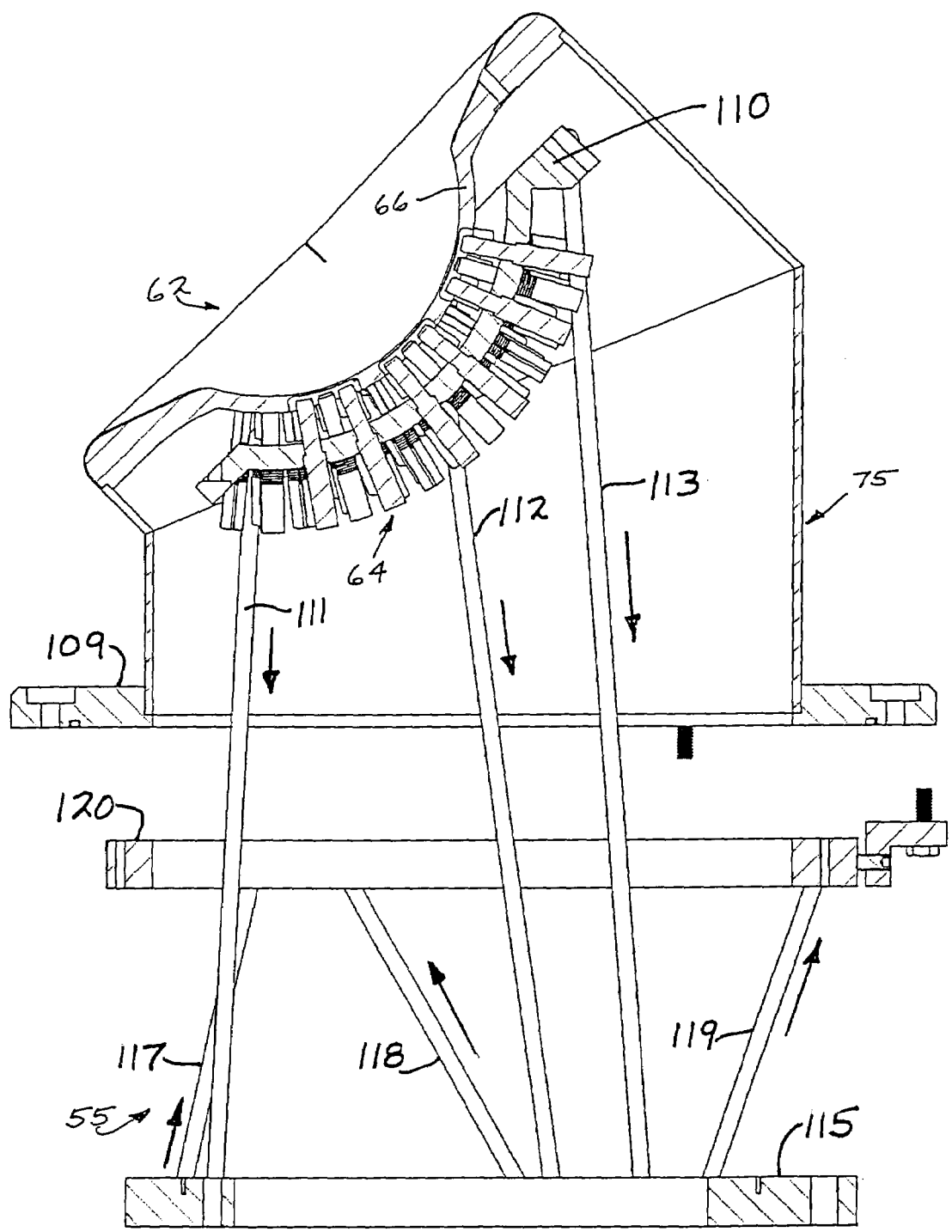
FIG. 29 is an enlarged sectional side elevational view of the headrest assembly and its supporting structure.

Referring now to FIG. 29, the relative close spacing of the sensors 64 and the headrest 66, is maintained constant through various temperature changes of the dewar 75. In this regard, when the system 10 either cools down or warms up, the differences in the coefficient of thermal expansion of the various components may cause the small gap between the sensors 64 and the headrest 66 to change in an undesirable manner. Therefore, according to the disclosed embodiment of the present invention, the gap between the sensors and the headrest remains substantially constant as a result of the mounting structure for the headrest assembly 62.

A mounting ring 109 is fixed to the headrest assembly 62 and mounts it fixedly to the dewar 75 in a rigid manner. A coil array plate 110 supports the sensors 64 in close proximity to the headrest 66 as hereinbefore described. A set of rods such as the rods 111, 112 and 113 support the plate 110 from below and have their lower ends connected to an intermediate mounting ring 115. A set of shorter rods such as the rods 117, 118, 119 support the intermediate mounting ring 115 from above and are connected to a fixed mounting ring 122. In this regard, the mounting ring 122 is fixed with respect to the dewar 75. The longer rods such as the rod 111 is composed of suitable material such as quartz so that when the system 10 cools down, the quartz rods shrink in length to pull the coil array plate 110 away from the headrest 66 to thereby increase lift-off. However, the shorter rods such as the rod 117 are also composed of suitable material such as quartz so that when the system cools down, for example, the quartz rods such as the rod 117 shrinks in length to pull the coil toward the headrest 66. In this regard, the longer and shorter rods compensate one another for temperature changes to help maintain a constant gap between the sensors and the headrest.

The rods are composed of quartz material since quartz has a low characteristic of thermal contraction between room temperature and cryogenic temperatures. Additionally, the coil array plate 110 is pre-adjusted to correct lift-off when the system is warm.

While particular embodiments of the present invention have been disclosed, it is to be understood that various different modifications and combinations are possible and are contemplated within the true spirit and scope of the invention. There is no intention, therefore, of limitations to the exact disclosure herein presented.

What is claimed is:

1. A magnetoencephalography system, comprising:
a portable cart for moving along the ground;

a SQUID dewar containing liquid helium mounted in an inverted manner on the cart;

a headrest assembly mounted on the cart and having a headrest with a honeycomb supporting structure for supporting a head of a patient and forming a portion of the dewar;

the headrest assembly includes an array of magnetic sensors of the SQUID dewar for responding to electrical activity of the brain of the head, the sensors at least partially disposed within the honeycomb structure; and a patient bed mounted on the cart adjacent to the headrest for supporting the body of the patient with his or her head supported by the headrest.

2. A magnetoencephalography system according to claim 1, wherein said headrest is concave and is configured in an ellipsoid shape having a sagittaf radius of curvature of between about 80 millimeters and about 120 millimeters for the sagittal axis of the head and having a coronal radius of curvature of between about 60 millimeters and about 90 millimeters at the coronal axis of the head.

3. A magnetoencephalography system according to claim 2, wherein the sagittal radius is between about 90 millimeters and about 110 millimeters, and wherein the coronal radius is between about 70 millimeters and about 80 millimeters.

4. A magnetoencephalography system according to claim 3, wherein said sagittal radius is about 100 millimeters, and wherein the coronal radius is about 75 millimeters.

5. A magnetoencephalography system according to claim 1, wherein the headrest is composed of non-metallic head-insulating structurally strong material.

6. A magnetoencephalography system according to claim 5, wherein said material is G-10 fiberglass.

7. A magnetoencephalography system according to claim 1, wherein each one of said sensors is disposed at a spacing distance from the outer head engaging surface of between about one millimeter and about three millimeters.

8. A magnetoencephalography system according to claim 7, wherein said spacing distance is between about one millimeter and about two millimeters.

9. A magnetoencephalography system according to claim 1, wherein each one of said sensors is disposed at a spacing distance of greater than about one millimeter from the outer head engaging surface of the headrest assembly.

10. A magnetoencephalography system according to claim 1, wherein each one of said sensors is a superconducting gradiometer having a pick-up coil diameter of between about four millimeters and about eight millimeters.

11. A magnetoencephalography system according to claim 10, wherein said pick-up coil diameter of between about five millimeters and about seven millimeters.

12. A magnetoencephalography system according to claim 11, wherein said pick-up diameter is about six millimeters.

13. A magnetoencephalography system according to claim 11, wherein each one of said sensors is a superconducting gradiometer having a pick-up coil, said sensors being substantially uniformly distributed relative to the head engageable surface of the headrest, each one of the sensor pick-up coils being spaced apart by a spacing distance of between about 6 millimeters and about 14 millimeters.

14. A magnetoencephalography system according to claim 13, wherein said spacing distance is between about 8 millimeters and about 12 millimeters.

15. A magnetoencephalography system according to claim 13, wherein said sensors are arranged in groups of four, wherein the spacing distance between adjacent sensors of a group is about 8.5 millimeters and the spacing distance between diagonally disposed sensors of a group is about 12 millimeters.

16. A magnetoencephalography system according to claim 1, wherein said sensors are arranged in groups thereof, and wherein said headrest has a corresponding series of recesses in the rear surface thereof positioned opposite to said groups of said sensors.

17. A magnetoenoephalography system according to claim 16, wherein each one of said recesses is dimensioned to the approximate size of its group of sensors.

18. A magnetoencephalography system according to claim 17, wherein said recesses are arranged in the honeycomb structure of the headrest.

19. A magnetoencephalography system according to claim 18, wherein each one of said group comprises four sensors.

20. A magnetoencephalography system according to claim 1, wherein said sensors are arranged in groups of four, each one of said four sensors of a group provides a separate communication channels the channels being useable individually, or combined or subtracted.

21. A magnetoencephalography system according to claim 1, wherein said cart includes electronic equipment for data acquisition from said sensors, and further including a container composed of conductive material for confining said electronic equipment to shield it from radio frequency interference.

22. A magnetoencephalography system according to claim 21, wherein said dewar has an external coating of conductive material for radio frequency interference shielding.

23. A magnetoencephalography system according to claim 21, further including a direct current power supply for supplying electrical power to said electronic equipment.

24. A magnetoencephalography system according to claim 23, further including a trailer having said power supply mounted thereon and being connected mechanically to said cart.

25. A magnetoencephalography system according to claim 1, wherein said array is an array of closely-spaced evenly-distributed cryocooled superconducting sensors disposed adjacent to the headrest for responding to electrical activity of the brain of the head, the sensors are cryocooled using liquid helium.

* * * * *

UNITED STATES PATENT AND TRADEMARK OFFICE
CERTIFICATE OF CORRECTION

PATENT NO. : 7,130,675 B2
APPLICATION NO. : 10/608725
DATED : October 31, 2006
INVENTOR(S) : Anthony P. Ewing et al.

It is certified that error appears in the above-identified patent and that said Letters Patent is hereby corrected as shown below:

Claim 1, column 25, line 16, delete "sagittaf" and insert -- sagittal --
Claim 13, column 25, line 56, delete "11" and insert -- 1 --
Claim 20, column 26, line 31, delete "channels" and insert -- channel --

Signed and Sealed this

Twenty-seventh Day of May, 2008

JON W. DUDAS
*Director of the United States Patent and Trademark Office*